(12) United States Patent
Ross

(10) Patent No.: US 12,073,014 B2
(45) Date of Patent: *Aug. 27, 2024

(54) VOICE BLANKING MUSCLE MOVEMENT CONTROLLED SYSTEMS

(71) Applicant: Hourglass Medical LLC, Monticello, IL (US)

(72) Inventor: Jeremy B. Ross, Monticello, IL (US)

(73) Assignee: Hourglass Medical LLC, Monticello, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/299,604

(22) Filed: Apr. 12, 2023

(65) Prior Publication Data

US 2023/0244303 A1 Aug. 3, 2023

Related U.S. Application Data

(63) Continuation of application No. 17/659,733, filed on Apr. 19, 2022, now Pat. No. 11,662,804.
(Continued)

(51) Int. Cl.
*G06F 3/01* (2006.01)
*G06F 3/16* (2006.01)
(Continued)

(52) U.S. Cl.
CPC .............. *G06F 3/011* (2013.01); *G06F 3/167* (2013.01); *G10L 17/22* (2013.01); *G10L 25/18* (2013.01)

(58) Field of Classification Search
CPC ....................................................... H04W 4/10
See application file for complete search history.

(56) References Cited

U.S. PATENT DOCUMENTS 3,227,836 A 1/1966 Renwick, Sr.
4,920,466 A 4/1990 Liu
(Continued)

FOREIGN PATENT DOCUMENTS

CA 2268980 A1 4/1998
CN 208338996 U 1/2019
(Continued)

OTHER PUBLICATIONS

"Detent", Merriam-Webster, definition, downloaded Jan. 23, 2024, from https://www.merriam-webster.com/ dictionary/detent, 14 pgs.
(Continued)

*Primary Examiner* — Shaheda A Abdin
(74) *Attorney, Agent, or Firm* — Ascenda Law Group, PC

(57) ABSTRACT

Systems for operating a controlled device via a wearable activation accessory that includes a sensor configured to detect relaxed and flexed conditions of muscles associated with clenching, flexing, and/or lateral displacement of a wearer's muscle, thereby allowing the wearer to generate control signals for a controlled element. The sensor is coupled to a controller, which has an output coupled to a control signal interface. The controller is programmed to receive and evaluate input signals from the sensor to determine whether or not they represent a command for the controlled device by assessing the input signals for a signal pattern indicative of a plurality of volitional muscle motion actions of a wearer of the wearable activation accessory. If/when the processor determines that the input signals represent a valid command, it decodes the command and transmits an associated control signal to the controlled device via the control signal interface.

12 Claims, 12 Drawing Sheets

Related U.S. Application Data

(60) Provisional application No. 63/261,052, filed on Sep. 9, 2021, provisional application No. 63/232,084, filed on Aug. 11, 2021, provisional application No. 63/201,280, filed on Apr. 21, 2021.

(51) Int. Cl.
   *G10L 17/22* (2013.01)
   *G10L 25/18* (2013.01)

(56) References Cited

U.S. PATENT DOCUMENTS

| | | | |
|---|---|---|---|
| 4,970,589 A | 11/1990 | Hanson et al. | |
| 5,083,246 A | 1/1992 | Lambert | |
| 5,226,712 A | 7/1993 | Luca | |
| 5,946,071 A | 8/1999 | Feldman | |
| 5,951,141 A | 9/1999 | Bradley | |
| 6,016,160 A | 1/2000 | Coombs et al. | |
| 6,046,712 A | 4/2000 | Beller et al. | |
| 6,126,294 A | 10/2000 | Koyama et al. | |
| 6,560,029 B1 | 5/2003 | Dobbie et al. | |
| 6,612,695 B2 | 9/2003 | Waters | |
| 6,896,389 B1 | 5/2005 | Paul | |
| 7,184,903 B1 | 2/2007 | Williams et al. | |
| 7,303,303 B1 | 12/2007 | Haynes | |
| 7,580,028 B2 | 8/2009 | Jeong et al. | |
| 7,814,903 B2 | 10/2010 | Osborne et al. | |
| 8,188,937 B1 | 5/2012 | Amafuji et al. | |
| 8,337,014 B2 | 12/2012 | Kokonaski et al. | |
| 8,587,514 B2 | 11/2013 | Lundstrom | |
| 8,708,483 B2 | 4/2014 | Kokonaski et al. | |
| 9,013,264 B2 | 4/2015 | Parshionikar et al. | |
| 9,285,609 B1 | 3/2016 | Rost | |
| 9,632,318 B2 | 4/2017 | Goto et al. | |
| 10,477,298 B2 | 11/2019 | Cruz-Hernandez | |
| 10,736,560 B2 | 8/2020 | Haugland et al. | |
| 2002/0027777 A1 | 3/2002 | Takasu | |
| 2002/0122014 A1 | 9/2002 | Rajasingham | |
| 2003/0202341 A1 | 10/2003 | McClanahan | |
| 2004/0008158 A1 | 1/2004 | Chi et al. | |
| 2004/0136178 A1 | 7/2004 | Yu | |
| 2004/0189930 A1 | 9/2004 | Skuro | |
| 2004/0252487 A1 | 12/2004 | McCullough et al. | |
| 2005/0102133 A1 | 5/2005 | Rees | |
| 2005/0105285 A1 | 5/2005 | Maden | |
| 2005/0226433 A1 | 10/2005 | McClanahan | |
| 2006/0048286 A1 | 3/2006 | Donato | |
| 2006/0061544 A1 | 3/2006 | Min et al. | |
| 2006/0119539 A1 | 6/2006 | Kato et al. | |
| 2006/0238878 A1 | 10/2006 | Miyake et al. | |
| 2007/0243835 A1 | 10/2007 | Zhu et al. | |
| 2007/0277819 A1 | 12/2007 | Osborne et al. | |
| 2008/0216215 A1 | 9/2008 | Lee | |
| 2009/0073082 A1 | 3/2009 | Yoshikawa | |
| 2009/0187124 A1* | 7/2009 | Ludlow | A61H 23/00 601/47 |
| 2009/0251661 A1 | 10/2009 | Fuziak, Jr. | |
| 2009/0267805 A1 | 10/2009 | Jin et al. | |
| 2010/0014699 A1 | 1/2010 | Anderson et al. | |
| 2010/0081895 A1 | 4/2010 | Zand | |
| 2010/0177277 A1 | 7/2010 | Kokonaski et al. | |
| 2010/0250231 A1 | 9/2010 | Almagro | |
| 2010/0271588 A1 | 10/2010 | Kokonaski et al. | |
| 2010/0283412 A1 | 11/2010 | Baudou | |
| 2010/0327028 A1 | 12/2010 | Nakabayashi et al. | |
| 2011/0089207 A1 | 4/2011 | Tricoukes et al. | |
| 2011/0221672 A1 | 9/2011 | Osterhout et al. | |
| 2011/0288445 A1 | 11/2011 | Lillydahl et al. | |
| 2011/0317402 A1 | 12/2011 | Cristoforo | |
| 2012/0002046 A1 | 1/2012 | Rapoport et al. | |
| 2012/0052469 A1* | 3/2012 | Sobel | G06F 3/011 434/262 |
| 2012/0127420 A1 | 5/2012 | Blum et al. | |
| 2012/0127423 A1 | 5/2012 | Blum et al. | |
| 2012/0206323 A1 | 8/2012 | Osterhout et al. | |
| 2012/0229248 A1 | 9/2012 | Parshionikar et al. | |
| 2012/0242698 A1 | 9/2012 | Haddick et al. | |
| 2012/0262667 A1 | 10/2012 | Willey | |
| 2012/0287284 A1 | 11/2012 | Jacobsen et al. | |
| 2012/0312669 A1 | 12/2012 | Breeds et al. | |
| 2013/0016426 A1 | 1/2013 | Chiang | |
| 2013/0201439 A1 | 8/2013 | Kokonaski et al. | |
| 2013/0278881 A1 | 10/2013 | Kokonaski et al. | |
| 2013/0300649 A1 | 11/2013 | Parkinson et al. | |
| 2013/0329183 A1 | 12/2013 | Blum et al. | |
| 2014/0000014 A1 | 1/2014 | Redpath et al. | |
| 2014/0028966 A1 | 1/2014 | Blum et al. | |
| 2014/0079257 A1 | 3/2014 | Ruwe et al. | |
| 2014/0082587 A1 | 4/2014 | Delaney | |
| 2014/0160250 A1 | 6/2014 | Pomerantz et al. | |
| 2014/0249354 A1 | 9/2014 | Anderson et al. | |
| 2014/0259287 A1 | 9/2014 | Waters et al. | |
| 2014/0259319 A1 | 9/2014 | Ross et al. | |
| 2014/0354397 A1 | 12/2014 | Quintal, Jr. et al. | |
| 2015/0094715 A1 | 4/2015 | Laufer et al. | |
| 2015/0109769 A1 | 4/2015 | Chang | |
| 2016/0054570 A1 | 2/2016 | Bosveld et al. | |
| 2016/0178903 A1 | 6/2016 | Nakajima | |
| 2016/0216519 A1 | 7/2016 | Park et al. | |
| 2016/0255305 A1 | 9/2016 | Ritchey et al. | |
| 2016/0313801 A1 | 10/2016 | Wagner et al. | |
| 2016/0316181 A1 | 10/2016 | Hamra | |
| 2017/0075198 A1 | 3/2017 | Kuroki | |
| 2017/0215717 A1 | 8/2017 | Orringer et al. | |
| 2017/0227780 A1 | 8/2017 | Tatsuta et al. | |
| 2017/0257723 A1 | 9/2017 | Morishita et al. | |
| 2017/0270820 A1 | 9/2017 | Ashby | |
| 2017/0322641 A1 | 11/2017 | Osterhout | |
| 2018/0003764 A1 | 1/2018 | Menon et al. | |
| 2018/0242908 A1 | 8/2018 | Sazonov et al. | |
| 2019/0142349 A1* | 5/2019 | Schorey | A61B 5/11 600/546 |
| 2019/0178476 A1 | 6/2019 | Ross | |
| 2019/0178477 A1 | 6/2019 | Ross | |
| 2019/0265802 A1 | 8/2019 | Parshionikar | |
| 2020/0059467 A1 | 2/2020 | Chereshnev | |
| 2020/0072596 A1 | 3/2020 | Pang et al. | |
| 2020/0097084 A1* | 3/2020 | Ross | A42B 3/303 |
| 2020/0249752 A1 | 8/2020 | Parshionikar | |
| 2020/0285080 A1 | 9/2020 | Belli et al. | |
| 2020/0320412 A1 | 10/2020 | Gillian et al. | |
| 2021/0029435 A1 | 1/2021 | Siahaan et al. | |
| 2022/0007154 A1* | 1/2022 | Ross | H04W 4/10 |

FOREIGN PATENT DOCUMENTS

| | | |
|---|---|---|
| DE | 10 2006 015334 A1 | 10/2007 |
| EP | 1 928 296 B1 | 5/2011 |
| FR | 2832906 A1 | 6/2003 |
| JP | 2002268815 A | 9/2002 |
| JP | 2009116609 A | 5/2009 |
| WO | WO 96/37730 A1 | 11/1996 |
| WO | WO 2004/087258 A1 | 10/2004 |
| WO | 2009/133258 A1 | 11/2009 |
| WO | WO 2010/062479 A1 | 6/2010 |
| WO | WO 2014/068371 A1 | 5/2014 |
| WO | WO 2015/124937 A1 | 8/2015 |
| WO | WO 2017/065663 A1 | 4/2017 |
| WO | WO 2020/117597 A1 | 6/2020 |
| WO | WO 2020/248778 A1 | 12/2020 |
| WO | WO 2022/098973 A1 | 5/2022 |

OTHER PUBLICATIONS

International Search Report and Written Opinion mailed Jan. 22, 2024, from the ISA/US, for International Application No. PCT/US23/32656 (filed Sep. 13, 2023), 13 pgs.

Gu; et al. "Efficacy of biofeedback therapy via a mini wireless device on sleep bruxism contrasted with occlusal splint: a pilot study", Journal of Biomedical Research, 2015, 29(2):160-168.

(56) References Cited

OTHER PUBLICATIONS

Communication pursuant to Article 94(3) EPC dated Apr. 28, 2023, from the European Patent Office, for European Patent Application No. 19827960.6, 7 pgs.
Office Action dated Apr. 24, 2023, for U.S. Appl. No. 18/146,087 (filed Dec. 23, 2022), 11 pgs.
Etani, Takehito, "The Masticator", The Masticator: the social mastication (2016), downloaded from: http://www.takehitoetani.com/masticator, 5 pages.
Goel, Mayank; et al., "Tongue-in-Cheek: Using Wireless Signals to Enable Non-Intrusive and Flexible Facial Gestures Detection", HMDs & Wearables to Overcome Disabilities, CHI 2015, Apr. 18-23, 2015, Crossings, Seoul, Korea, pp. 255-258.
International Preliminary Report on Patentability mailed Mar. 3, 2021, from the IPEA/US, for International Patent Application No. PCT/US2019/063717 (filed Nov. 27, 2019), 6 pgs.
International Preliminary Report on Patentability mailed Aug. 4, 2020, from the IPEA/US, for International Application No. PCT/US2018/062767 (filed Nov. 28, 2018), 18 pgs.
International Preliminary Report on Patentability mailed Jan. 12, 2023, from The International Bureau of WIPO, for International Patent Application No. PCT/US2021/039395 (filed Jun. 28, 2021), 11 pgs.
International Search Report and Written Opinion mailed Mar. 5, 2019, from the ISA/US, for International Application No. PCT/US18/62767 (filed Nov. 28, 2018), 15 pages.
International Search Report and Written Opinion mailed May 13, 2020, from the ISA/European Patent Office, for International Application No. PCT/US2019/063717 (filed Nov. 27, 2019), 16 pgs.
International Search Report and Written Opinion mailed Apr. 20, 2022, from the ISA/European Patent Office, for International Patent Application No. PCT/US2022/012746 (filed Jan. 18, 2022), 15 pgs.
International Search Report and Written Opinion mailed Oct. 20, 2021, from the ISA/European Patent Office, for International Application No. PCT/US2021/039395 (filed Jun. 28, 2021), 14 pgs.
International Search Report and Written Opinion mailed Jan. 25, 2022, from the ISA/European Patent Office, for International Application No. PCT/US2021/058209 (filed Nov. 5, 2021), 15 pgs.
International Search Report and Written Opinion mailed Jul. 26, 2022, from the ISA/European Patent Office, for International Patent Application No. PCT/US2022/025324 (filed Apr. 19, 2022), 13 pgs.
Invitation to Pay Additional Fees and Partial Search mailed Mar. 4, 2020, from the ISA/European Patent Office, for International Patent Application No. PCT/US2019/063717 (filed Nov. 27, 2019), 15 pages.
Khoshnam; et al., "Hands-Free EEG-Based Control of a Computer Interface Based on Online Detection of Clenching of Jaw", International Conference on Bioinformatics and Biomedical Engineering, IWBBIO 2017, Part I, Lecture Notes in Computer Science book series (LNCS, vol. 10208), pp. 497-507.
Knapp, R. Benjamin, "Biosignal Processing in Virtual Reality Applications," Cal. State University Northridge Center on Disabilities Virtual Reality Conference 1993 (1993) (available at http://www.csun.edu/~hfdss006/conf/1993/proceedings/BIOSIG~1.htm).
Tato-Klesa, Hella, "Detection of Teeth Grinding and Clenching using Surface Electromyography", Master's thesis, Jul. 29, 2020, Technische Universität München, Munich, Germany, 72 pgs.
Terndrup, Matthew, "Wiggle your nose to control VR experiences with Reach Bionics," Upload VR (Jan. 12, 2016) (Available at https://uploadvr.com/reach-bionics-lets-you-control-vr-experiences-by-wiggling-your-nose/).
Von Rosenberg; et al., "Smart helmet: Monitoring brain, cardiac and respiratory activity," 2015 37th Annual International Conference of the IEEE Engineering in Medicine and Biology Society (EM BC), Milan, 2015, pp. 1829-1832, NPL001 (Year: 2015).
Xu; et al., "Clench Interaction: Novel Biting Input Techniques", Human Factors in Computing Systems Proceedings (CHI 2019), May 4-9, 2019, 12 pages.

\* cited by examiner

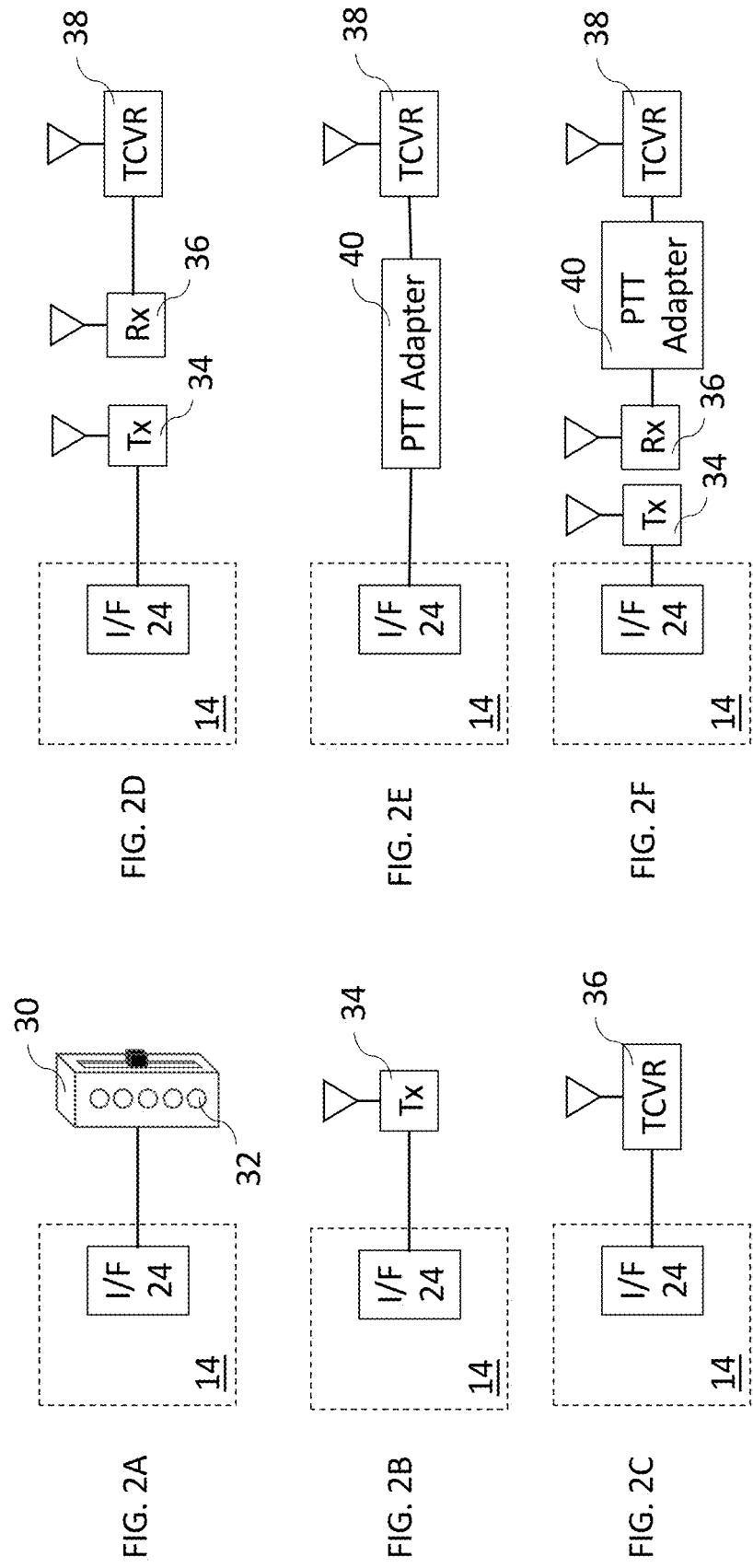

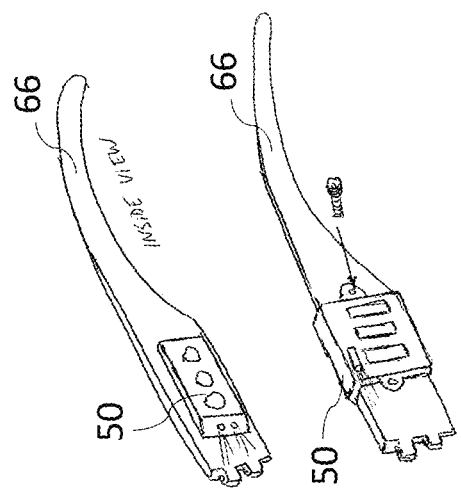
FIG. 5
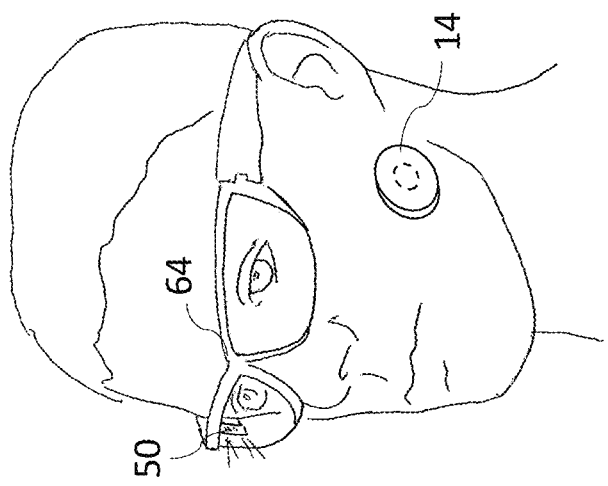
FIG. 6
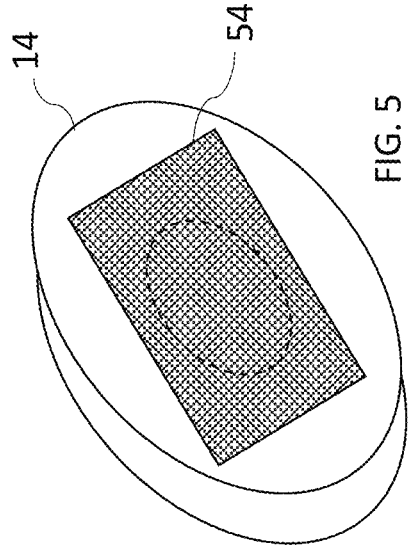
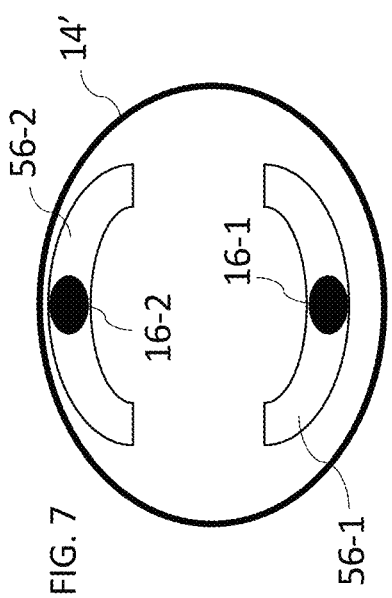
FIG. 7

VOICE BLANKING MUSCLE MOVEMENT CONTROLLED SYSTEMS

RELATED APPLICATIONS

This is a CONTINUATION of U.S. patent application Ser. No. 17/659,733, filed 19 Apr. 2022, which is a NON-PROVISIONAL of, claims priority to, and incorporates by reference U.S. Provisional Application Nos. 63/201,280, filed 21 Apr. 2021, 63/232,084, filed 11 Aug. 2021, and 63/261,052, filed 9 Sep. 2021.

FIELD OF THE INVENTION

The present invention relates to systems and methods for operating a controlled device in a hands-free manner through volitional muscle motions of a wearer, including systems and methods for improving the accuracy and overall performance of hands-free actuation and control of head-worn devices provided by masseter muscle and other maxillofacial movements.

BACKGROUND

Simple head-worn devices such as surgical and outdoor recreational headlamps, and more advanced systems such as audio headphones and virtual reality headsets have used input means such as tactile buttons and switches, touch activated control surfaces, and gesturing technologies, that might also rely on head and eye tracking technologies, as means of controlling their operation. All of these input means require a user to use his or her hands to effect input to the device. Advancements in hands-free functionality for such devices have been limited primarily to voice recognition technologies that have limitations when used in noisy or sound-sensitive environments or eye tracking technologies that require the user to gaze at particular objects in order to be detected, which requires "dwell time," increasing input latency.

BRIEF DESCRIPTION OF THE DRAWINGS

The present invention is illustrated by way of example, and not limitation, in the figures of the accompanying drawings, in which:

FIGS. 2A-2F illustrate examples of devices operated under the control of an activation accessory configured in accordance with an embodiment of the present invention.

FIG. 5 illustrates an example of an activation accessory having a film of adhesive on one surface for attachment to a wearer.

FIG. 6 illustrates an example of an activation accessory such as that shown in FIG. 5 as secured to the face of a wearer by adhesive.

FIG. 7 illustrates an example of an activation accessory for a controlled device configured with multiple sensors, in accordance with an embodiment of the present invention

DETAILED DESCRIPTION

Figure 1:
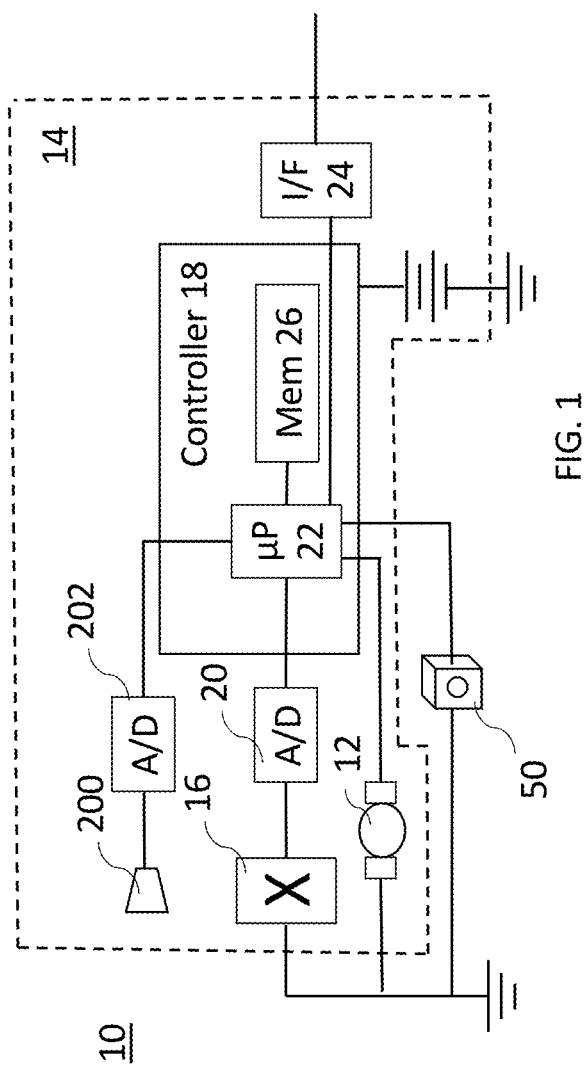
FIG. 1 illustrates an example of an activation accessory for a controlled device configured in accordance with an embodiment of the present invention.

Described herein are systems and methods for hands-free operation of controlled devices, for example illumination systems, push-to-talk systems, and other devices. These systems and methods are characterized, in part, by employing a switch or switch element, e.g., a Hall effect or other sensor, that is positioned on or near the face of a user, for example, overlying an area of the user's jaw, chin, masseter muscle, or another area of the face or head, such as the temple, so that clenching, flexing, and/or lateral displacement of the user's jaw and/or movement of the jaw, whether side to side or otherwise, for example by manipulation of the masseter muscle, medial pterygoid muscle, lateral pterygoid muscle (or a combination thereof), and/or other maxillofacial movements, activate or deactivate the switch or switch element. In one embodiment, the switch or switch element is employed in combination with a headset, eyeglasses, visor, or mask, etc., suitable for wear in a variety of contexts, including military, law enforcement, health care, and others (e.g., consumer). The headset, eyeglasses, visor, or mask, etc., positions the switch or switch element so that it overlies the wearer's jaw, e.g., the masseter muscle or a portion thereof, or the medial or lateral pterygoid muscle, or the mandible, chin, or another area of the wearer's face or head, such as the temple, so that clenching, flexing, and/or lateral displacement of the wearer's jaw (or a combination thereof) activates the switch or switch element, or positions the switch or switch element near the wearer's face so that clenching, flexing, and/or lateral displacement of the wearer's jaw (or a combination thereof) can be observed, e.g., by optical or proximity sensors, and the observation of the movement used to activate the switch or switch element, in either or both instances thereby allowing for hand-free operation of the controlled device. Other embodiments of the invention make use of the switch or switch element as part of other head-worn illumination, imaging, and/or communication systems. In some instances, the switch or switch element may be positioned in locations that allow for activation/deactivation of the switch or switch element by means of manipulation of muscles associated with a wearer's eyebrow, temple, etc. Note, the activation or deactivation of the switch or switch element is not as a result of any speech or other sound associated with the clenching, flexing, and/or lateral displacement of the wearer's jaw, but rather the movement of the jaw (or other part or parts of the wearer's face) as a result of such actions.

Reference to a switch or switch element herein is intended to mean one or more components of a switch, which may be a mechanical switch, an electrical switch, an electrotechnical switch, a virtual switch (e.g., one that is implemented in software running on a controller or other form of programmable device), etc. In cases where only a switch or switch element is referred to in the singular, it should be understood that either or both are intended. Activation of a switch or switch element may, in various embodiments, be effected by moving one component thereof relative to one or more other components thereof, e.g., through one or more volitional muscle movements.

One embodiment of the present invention provides a system and method for improving the accuracy and overall performance of hands-free actuation and control of devices provided by masseter muscle and/or other maxillofacial movements. These systems and methods are characterized, in part, by employing a switch or switch element that is positioned on or near a user, for example, overlying one or more muscles of the wearer. Particular embodiments of the invention refer to a switch or switch element that is positioned on or near a wearer's jaw, chin, or another area of the wearer's face or head, such as the temple, so that clenching, flexing, and/or lateral displacement of the wearer's jaw, for example by manipulation of the masseter muscle, medial pterygoid muscle, and/or lateral pterygoid muscle (or a combination thereof), activates or deactivates the switch or switch element. However, the present invention also concerns more broadly positing a switch/switch element so that it can be activated, deactivated, or otherwise controlled by movement, clenching, unclenching, flexing, unflexing, or otherwise moving one or more muscles in an area of the wearer's body near, adjacent, underlying, or overlying the location at which the switch or switch element is positioned. Therefore, although much of the discussion herein refers to a switch or switch element positioned near a wearer's jaw, the reader should regard such descriptions as examples being made for convenience, and not as a limitation of the invention. In other embodiments, the switch or switch element may be placed on or near a wearer's arm, leg, torso, chest, hand, finger, foot, toe, temple, or other area of the wearer's body.

As used herein, when referencing an area of a wearer's face overlying the jaw or masseter muscle, as in a switch or switch element overlying such an area, it means a wearable module or a wearable device, such as a wearable electronic controller, has one or more surfaces, e.g., control surfaces (e.g., Hall effect sensors, electromyography (EMG) sensors, piezo switches, tape switches, fabric switches, etc.), positioned to contact the right and/or left side of the wearer's face, for example within an area below the ear canal to the bottom of the mandible and extending forward beneath the zygomatic arch, which is formed between the zygomatic process of the temporal bone and the temporal process of the zygomatic bone, and the zygomatic bone. The control surfaces may be switches and/or switch elements, or other control surfaces configured to detect a relaxed condition and a flexed/displaced condition of one or more muscles, e.g., the wearer's masseter muscle(s) (see, e.g., FIG. 9), thereby allowing the wearer to generate input signals for controlling electronic system components via muscle manipulation. Alternatively, or in addition, it may refer to a wearable module, wearable electronic controller, or other wearable element that is positioned to contact the right and/or left side of the wearer's face at or near the temple or above the eyebrow. Still further, it may refer to a wearable module, wearable electronic controller, or other wearable element that is positioned to contact the wearer's chin or another part of the wearer's body such as an arm, leg, torso, chest, hand, or foot. In any of these instances, the control surfaces are configured to detect (see, e.g., FIG. 9) a relaxed condition and a flexed condition of one or more muscles, e.g., muscles associated with clenching, flexing, and/or lateral displacement of the wearer's jaw or displacement of the jaw itself, thereby allowing the wearer to generate input signals for controlling electronic system components via such volitional muscle manipulation. The wearable module, wearable electronic controller, or other wearable element may be adjustable in terms of its positioning so that one or more of the active control surfaces are located within desired areas overlying a portion of the wearer's face or head and means for adjusting the contact pressure of the active control surfaces against the wearer's face or head may be provided. The wearable module, wearable electronic controller, or other wearable element may be constructed to house one or more of the electronic system components (e.g., lights, cameras, displays, laser pointers, a haptic engine in the form of a vibration motor, etc.) that is (are) being controlled by muscle manipulation.

In still further embodiments, the wearable module, wearable electronic controller, or other wearable element may be positioned so that physical contact of an active control surface with the wearer's body is unnecessary. For example, contactless sensors such as optical sensors which employ visible or infrared light or proximity sensors may be positioned about the user's body (e.g., mounted on eyeglasses, earphone cups, earbuds, headsets, headbands, visors, masks, nosepieces, etc.) and oriented to detect movement, e.g., clenching, flexing, and/or lateral displacement, of the user's jaw muscles or other muscle(s), for example by volitional manipulation of the masseter muscle, medial pterygoid muscle, and/or lateral pterygoid muscle (or a combination thereof). Detection of such motion may be used to activate or deactivate a switch that, in turn, activates or deactivates a controlled element, or the contactless sensor may itself be regarded as a switch element and used to send an input to a programmed controller, which in turn sends a signal to activate or deactivate a controlled element.

For much of the remainder of the discussion herein, the example of a switch that is positioned on or near a wearer's jaw, chin, or another area of the wearer's face or head is used, however, this is only for convenience and the present invention applies to a switch or switch element that overlies an area of the wearer's body so that clenching, flexing, and/or lateral displacement of the wearer's muscles at or near the area of the wearer's body (or a combination thereof) activates, deactivates, or otherwise operates the switch, or positions the switch near the wearer so that clenching, flexing, and/or lateral displacement of the muscles at or near the area of the wearer's body (or a combination thereof) can be observed, e.g., by optical or proximity sensors, and the observation of the movement used to activate, deactivate, or otherwise operates the switch, in either or both instances thereby allowing for hand-free operation of a controlled device.

The use of "clench interactions" has been recognized as a viable control technique. For example, the present applicant's U.S. PGPUB 2020/0097084, Xu et al., "Clench Interaction: Novel Biting Input Techniques," Proc. 2019 CHI Conference on Human Factors in Computing Systems (CHI 2019), May 4-9, 2019, Glasgow, Scotland UK, and Koshnam, E. K. et al., "Hands-Free EEG-Based Control of a Computer Interface based on Online Detection of Clenching of Jaw," in: Rojas I., Ortuño F. (eds) Bioinformatics and Biomedical Engineering, IWBBIO 2017, pp. 497-507 (Apr. 26-28, 2017) all provide examples of such techniques. In Xu et al., the use of bite force interfaces may afford some advantages in some applications, however, the present invention adopts a different approach inasmuch as it relies on sensors placed outside a user's oral cavity. Such sensors are more suitable for applications where the presence of sensors inside one's mouth may be uncomfortable or impractical. In Koshnam et al., the EEG sensors were external to the oral cavity, having been placed at temporal sites T7 and T8 on the wearer's head, but there was no provision for alerting the wearer when a command signal was recognized as having been initiated through a jaw clench action. Accordingly, the system was perceived as having excessive lag time in recognizing and implementing a clench action, which adversely impacted its use as a control element for a remote device.

Referring to FIG. 1, an example of an activation accessory 10 for a controlled device is shown. The activation accessory 10 includes an optional vibration motor 12, a wearable module 14 that includes a sensor 16 (e.g., a Hall effect sensor), and a controller 18. In some embodiments, when it is present the vibration motor 12 may also be included in wearable module 14. Sensor 16 is communicably coupled to controller 18 through an analog-to-digital (A/D) converter 20, which converts the analog output of the sensor 16 to a digital signal that is provided as an input to a processor 22 of the controller 18. In some cases, an A/D converter 20 will not be needed, e.g., where the output of the sensor 16 is already digitized, or it may be incorporated within controller 18. Processor 22, in turn, has outputs coupled to a control signal interface 24 and the vibration motor 12.

A Hall effect sensor is but one example of a sensor 16 that may be used in connection with activation accessory 10 and in other embodiments one or more such sensors, which may or may not be Hall effect sensors, may be used. Generally, sensor 16 is useful when the activation accessory 10 is to be in physical contact with the wearer, such as when it is on or near the wearer's face, as is the case for various embodiments of the invention as discussed herein. In other embodiments, sensor 16 may be any of an ultrasonic motion sensor, a camera or LIDAR unit, a motion sensor (e.g., employing one or more light emitting diodes for detection of motion), a laser sensor such as a vertical cavity surface emitting laser (VCSEL) sensor, or, more generally, a time of flight sensor that uses optical and/or acoustic means to detect motion. Or, sensor 16 may be another form of proximity or motion sensor. In such cases, sensor 16 need not be in physical contact with the wearer's face, and instead may be positionable so as to be able to detect movement, e.g., clenching, flexing, and/or lateral displacement, of the user's jaw, for example by volitional manipulation of the masseter muscle, medial pterygoid muscle, and/or lateral pterygoid muscle (or a combination thereof), temple, eyebrow, chin, or other aspect of the user's head or face. In these instances, the vibration motor 12 (which, when present, is used for haptic feedback to the user to indicate successful recognition of a command input) is likely not included in the same wearable module as the sensor 16 and instead may be contained in a separate module and worn apart from the sensor 16. Similarly, the sensor 16 may itself be worn separately from the controller 18 and other elements of the activation accessory 10. Therefore, the depiction of the wearable module 14 in dashed outline fashion should be understood as being optional and in some cases representing several different wearable modules that may be worn at different places on the user. For ease of reference, a single wearable module 14 will be described herein, but it should be remembered that this is for purposes of illustration only.

The processor 22 of controller 18 is also coupled to a memory 26, which stores processor-executable instructions that, when executed by processor 22, cause processor 22 to receive and evaluate input signals from the sensor 16. Controller 18 (i.e., processor 22) evaluates the input signals to determine whether or not they represent a command for the controlled device by assessing the input signals for a signal pattern indicative of a plurality of volitional jaw movements or other maxillofacial movements or actions of a wearer of the wearable module 14. As more fully discussed below, if/when the processor 22 determines that the input signals from sensor 16 represent a command for the controlled device, then processor 22 decodes the command and transmits an associated control signal to the controlled device (not shown in this view) via the control signal interface 24, as well as transmitting an activation signal to the vibration motor 12, if it is present. On the other hand, if the processor 22 determines that the input signals from sensor 16 do not represent the command for the controlled device, no control signal or activation signal is transmitted and processor 22 proceeds to evaluate further/new input signals from the sensor 16 in a like manner as the original input signals. In one embodiment, the activation signal for the vibration motor 12 is a pulse width modulated signal. The haptic feedback provided by vibration motor 12, e.g., in response to jaw clench/movement or other maxillofacial movement actions of a wearer, may also be activated by another user (e.g., through a communication to the wearer of wearable module 14) to provide a means for silent communication.

To improve the accuracy and overall performance of the activation accessory 10, means for blanking or otherwise ignoring input signals produced by maxillofacial movements that are involved when forming speech are provided. Maxillofacial movements that are involved when forming speech can result in command input patterns being inadvertently produced, thereby resulting in false input commands being generated by activation accessory 10. By audibly detecting such speech using decibel sensing, voice tone analysis, or other means via an integrated or remote/accessory microphone and ignoring all or a certain degree/range of maxillofacial movements when such audible speech is detected, inadvertent speech-generated input commands can be reduced or eliminated.

Accordingly, a microphone 200 and A/D converter 200 are provided as components of activation accessory 10. Although a microphone 200 integrated as a component of wearable module 14 is shown, a remote microphone and associated remote A/D converter may be used. Microphone 200 detects audible sounds, for example speech by the wearer of activation accessory 10, and produces an analog output in response to those sounds. The analog output is digitized by A/D converter 202 and provided as an input to processor 22. For example, processor 22 may periodically sample the output of A/D converter 202 and process the signal so output to determine if any wearer's speech is being detected by microphone 200. Appropriate filters may be employed to distinguish the wearer's speech from that of others and/or ambient noise. For example, since the wearer's speech would be expected to be louder than that of any others nearby, a threshold filter could be employed to distinguish the wearer's speech from that of others. Also, speech vs noise could be distinguished based on spectral content and/or other parameters.

Figure 15:
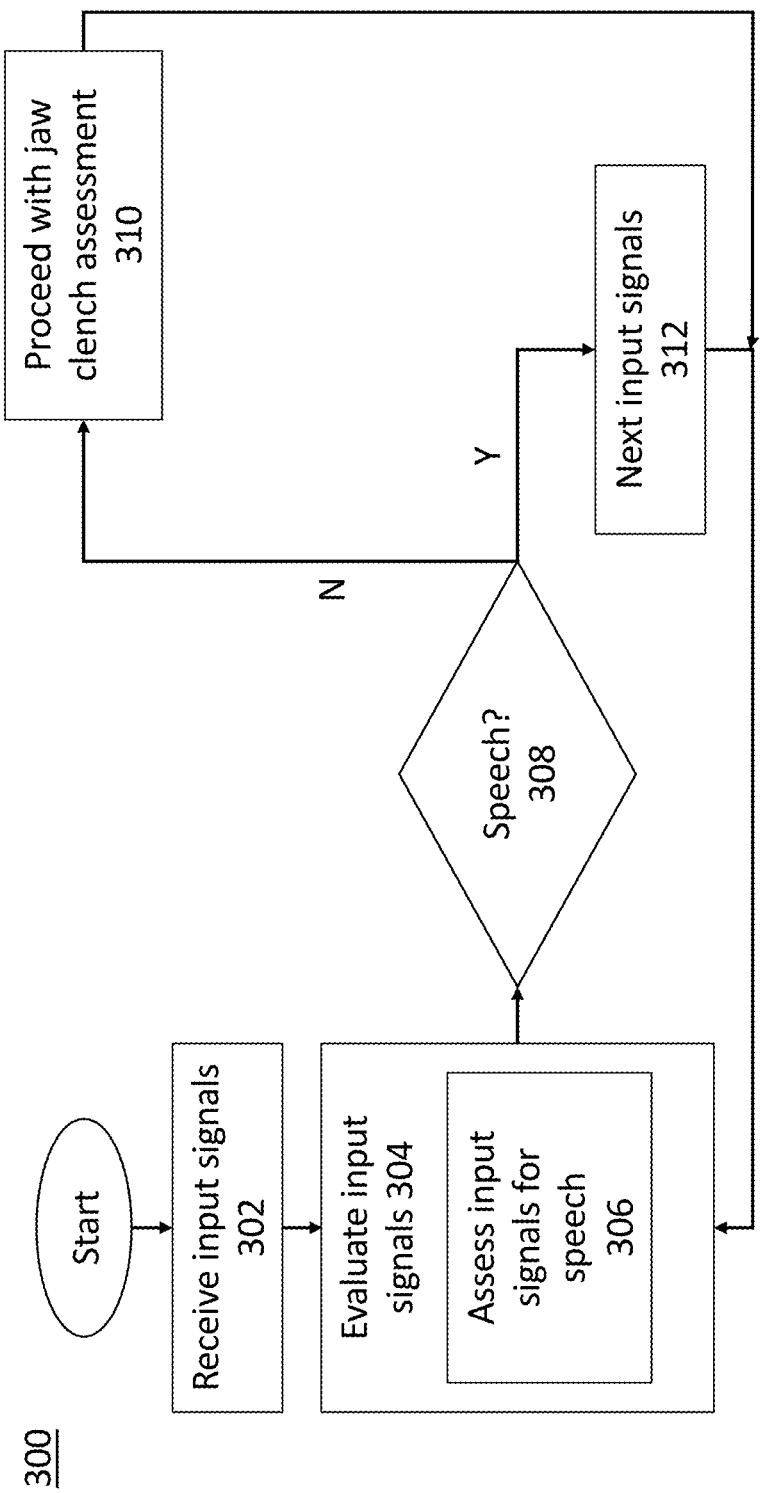
FIG. 15 illustrates a method of distinguishing volitional muscle actions of a wearer from wearer's speech in accordance with an embodiment of the invention.

FIG. 15 illustrates a method 300 of distinguishing wearer speech from volitional jaw movements in accordance with an embodiment of the invention. At 302, the controller 18 receives input signals from the microphone 200 in the wearable module 14 via A/D converter 202 along with other jaw movement inputs from the Hall effect or other sensor. At 304, processor 22 of controller 18 evaluates the microphone input signals according to and by executing processor-executable instructions stored in memory 26 to determine whether or not the input signals represent speech of the wearer. As discussed above, this evaluation proceeds by the processor assessing 306 the input signals for signal patterns, amplitudes, and or other indications suggestive of wearer speech or other vocalizations. If processor 22 determines that the input signals are not indicative of wearer speech, step 308, then processor 22 proceeds with other decoding operations to determine if a command input is being sensed 310. Such decoding operations are discussed further below. Otherwise, step 312, the processor 22 deems the jaw movement signals to be associated with wearer speech and does not further process the associated jaw movement signals and instead proceeds to evaluate next input signals 312 from the microphone and Hall effect sensor in a like manner as the first input signals.

Additionally, or alternatively, detection of a wearer's vocal cord activation when forming speech may be detected by tuned vibration sensors housed within a head-worn device associated with activation accessory 10 and/or by applying remote vibration sensors to the wearer's neck, jaw, or other location via wired or wireless connections. A blanking or false signal rejection method similar to that shown in FIG. 15 and described above may be employed for inputs provided by such sensors in order to reduce or eliminate false input commands caused by associated maxillofacial movements. Furthermore, in addition to or in lieu of a microphone, EMG sensors and/or integrated or remote cameras could be employed to detect an open or closed position of the wearer's mouth or tongue movement and manipulation during speech formation, yawning, or sneezing. Still further, other sensors such as highly sensitive pressure sensors could be used to detect air exhalation from the mouth. Input signals from both open mouth position sensors and air exhalation sensors could be used in a manner similar to that discussed above to eliminate false jaw clench input commands as neither would be detectable while clenching the jaw.

Beyond speech detection, embodiments of the invention may further provide speech recognition and/or voice recognition. Speech recognition involves, generally, the recognition and translation of spoken words. Various methods of speech recognition are known in the art, and many modern techniques employ Hidden Markov Models: statistical models that output sequences of symbols or quantities based on input speech signals. The speech signal, e.g., as provided by microphone 200, may be sampled by the controller and the samples applied as inputs to a Hidden Markov Model process running on the controller to produce an output sequence of vectors. These vectors are then used to identify associated phonemes, and the phonemes used to identify the most likely spoken words. Such systems can thus be used to interpret spoken commands for controlled devices, for example, commands not associated with non-speech related volitional jaw movements. Alternatively, or in addition, the controller may be configured to enhance a speech recognition process through decoding of the jaw movements associated with same through a process such as that used to decode commands made by volitional jaw movements. This may be effected by analyzing the signals produced by sensor 16 while the user is speaking, and correlating those signals with the outputs of a speech recognition process as a means of enhancing the likelihood of correctly identifying the spoken word(s).

Voice recognition, on the other hand, generally relates to speaker identification and may or may not include recognition of actual words that are spoken. In embodiments of the present invention, voice recognition may be employed to identify a user prior to executing and/or accepting commands made by the user, whether through volitional jaw movements or otherwise. Voice recognition may likewise include the controller sampling speech signals from microphone 200 and then using one or more pattern matching and/or other techniques to identify, with a specified probability, the identity of the speaker. If the speaker is confirmed, to a sufficient degree of likelihood, to be an authorized user of the activation accessory, the controller may permit execution of commands input by the user.

Beyond wearable technology devices, these voice/speech blanking methods could also be used to improve input signal processing for assistive PC control and navigation, and other system/device control for users with disabilities who currently rely on EMG sensors placed on the head or face that detect input signals while speaking that interfere with deliberate input generated by distinct, command-signal-generating, maxillofacial movements.

Regardless of the sensing technology and detection method used, embodiments of the present invention allow for more accurate activation of hands-free systems by ignoring the detection of maxillofacial movements as an input modality while the wearer is speaking and then immediately detecting maxillofacial movements again and processing them for system input commands once the wearer is no longer speaking.

In addition to voice/speech blanking, processor 22 may be programmed to execute one or more rules when wearer speech is detected and decoded. For example, while the procedures described above are employed for discriminating between actual command inputs by volitional jaw clench/movement and speech, in cases where speech is detected, processor 22 may be further configured to execute speech recognition routines to decode commands relayed by speech input and to thereafter issue signals to execute such commands. Similarly, processor 22 may be configured to execute voice recognition routines so as to ensure volitional jaw clench/movement commands are only executed by authorized wearers as determined through voice recognition of the wearer.

Referring now to FIGS. 2A-2F, various examples of controlled devices and arrangements for communicatively coupling same to the wearable module 14 are shown. In FIG. 2A, the controlled device is an illumination element 30 made up of one or more LEDs 32. As indicated above, the processor of controller 18 is coupled to the control signal interface 24 and is adapted to transmit a control signal to the controlled device, in this case illumination element 30, via the control signal interface 24. Not shown in the illustration are drivers and other interface elements that may be present to amplify and/or otherwise condition the control signal so that it is suitable for use with the illumination element 30.

FIG. 2B illustrates an example in which the wearable module 14 is coupled to a transmitter 34 via the control signal interface 24. Transmitter 34 may be a low power/short range transmitter, such as a Bluetooth™, Bluetooth Low Energy (BLE), Zigbee, infrared, WiFi HaLow (IEEE 802.22h) or other WiFi, Z-wave, Thread, SigFox, Dash7, or other transmitter. The transmitter 34 may itself be the controlled device or, alternatively, as shown in FIG. 2D, the transmitter 34 may be one component of a wireless communication system that includes a receiver 36 communicatively coupled to a controlled device, such as two-way radio 38. In such an arrangement, transmitter 34 is adapted for radio frequency communication with receiver 36 at the controlled device. Thus, the control signal issued by processor 22 of controller 18 is coupled to the control signal interface 24 and transmitted via a radio frequency signal from transmitter 34 to the controlled device.

FIG. 2C shows a further alternative in which the wearable module 14 is coupled directly to two-way radio 36. In this example, the control signal interface 24 may be coupled to the two-way radio 36 by a cable having a plug configured to mate with a jack at the two-way radio 36 (or, more generally, the controlled device). As such, the wearable module 14 may function as a push-to-talk (PTT) unit for the two-way radio 36 (or, more generally, an activation switch for the controlled device). Or, as shown in FIGS. 2E and 2F, the wearable module 14 may function as an ancillary PTT element for a PTT adapter 40 for the two-way radio 36 (or, more generally, the controlled device). The connection between the wearable module 14 (control signal interface 24) and the PTT adapter 40 may be wired, as shown in FIG. 2E, e.g., using a cable having a plug configured to mate with a jack at the PTT adapter, or wireless, using a transmitter/receiver pair 34, 36. Of course, other arrangements for communicating the control signal produced by the processor 22 (or, more generally, controller 18) of the wearable module 10 to a controlled device may be used.

In addition to the above-described examples, the processor 22 may also communicate with and control other peripherals, such as a heads-up display, audio input/output unit, off-headset unit, etc. Processor 22 is a hardware-implemented module and may be a general-purpose processor, or dedicated circuitry or logic, such as a field programmable gate array (FPGA) or an application-specific integrated circuit (ASIC)), or other form of processing unit. Memory 26 may be a readable/writeable memory, such as an electrically erasable programmable read-only memory, or other storage device.

Figure 3:
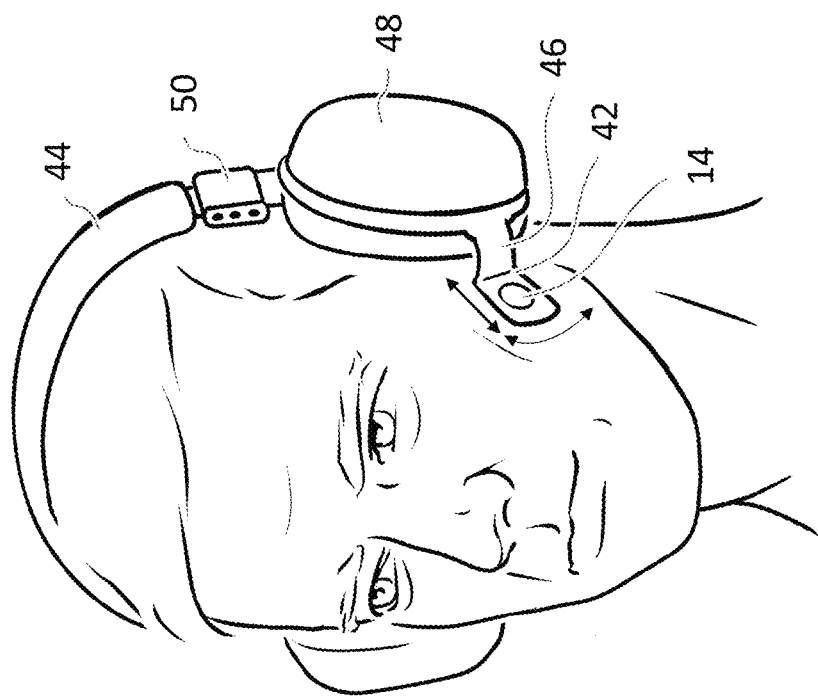
FIG. 3 illustrates an example of an activation accessory secured in a headset mount configured in accordance with an embodiment of the present invention.
Figure 8:
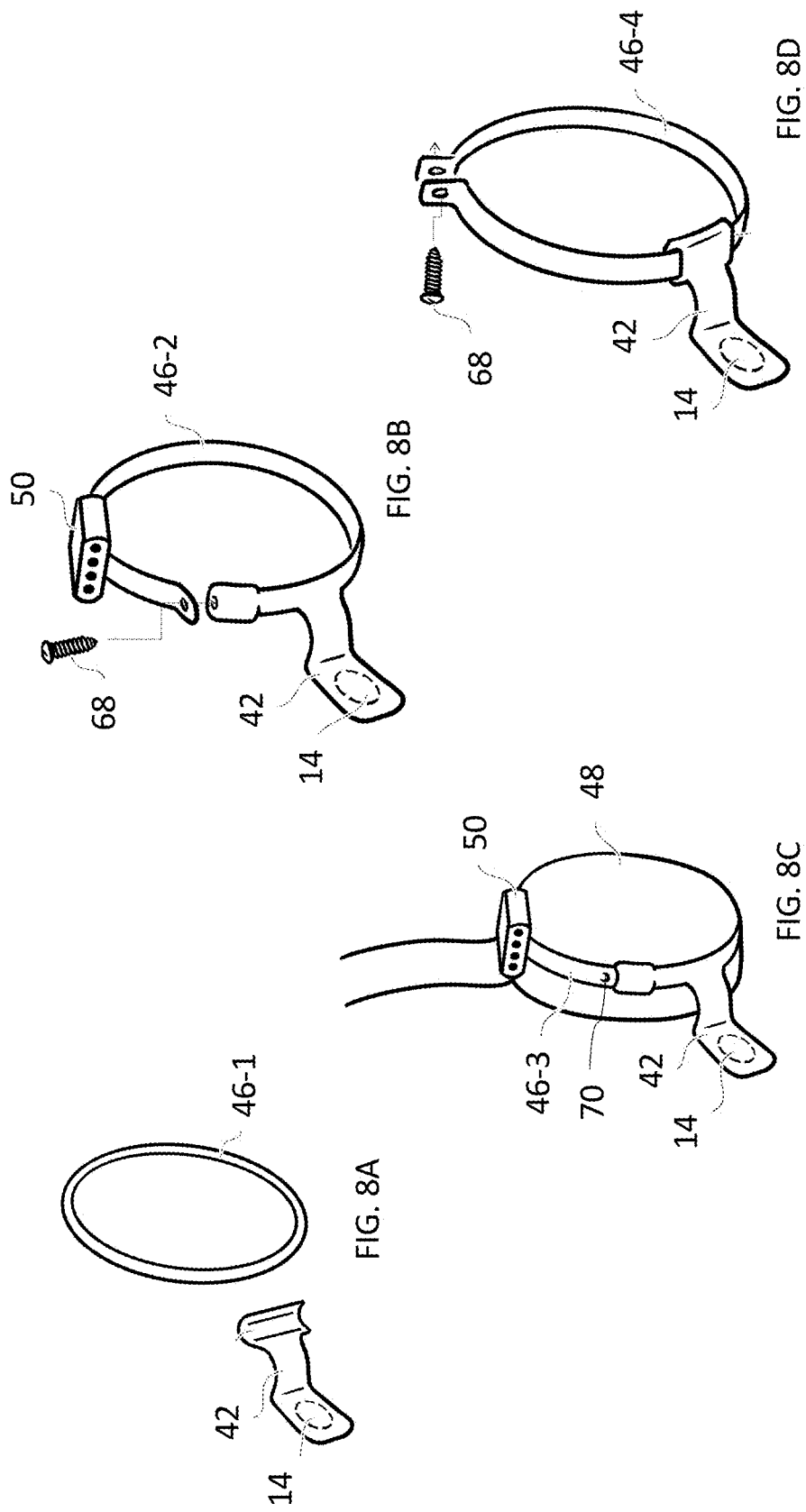
FIGS. 8A-8D show examples of arrangements for securing wearable module of an activation accessory to a headset earphone cup in accordance with embodiments of the present invention.

Referring now to FIG. 3, in various embodiments, the wearable module 10 may be supported in a mount 42 of a headset 44, or another arrangement. For example, such a mount 42 may be moveable with respect to a frame 46 of the headset or a component thereof, such as earcup 48, so as to permit locating the wearable module 14 at different positions on the wearer. More generally, such a mount 42 may be configured to position the wearable module 14 so as to be overlying an area of the wearer's jaw or other portion of the wearer's head or face.

Figure 4:
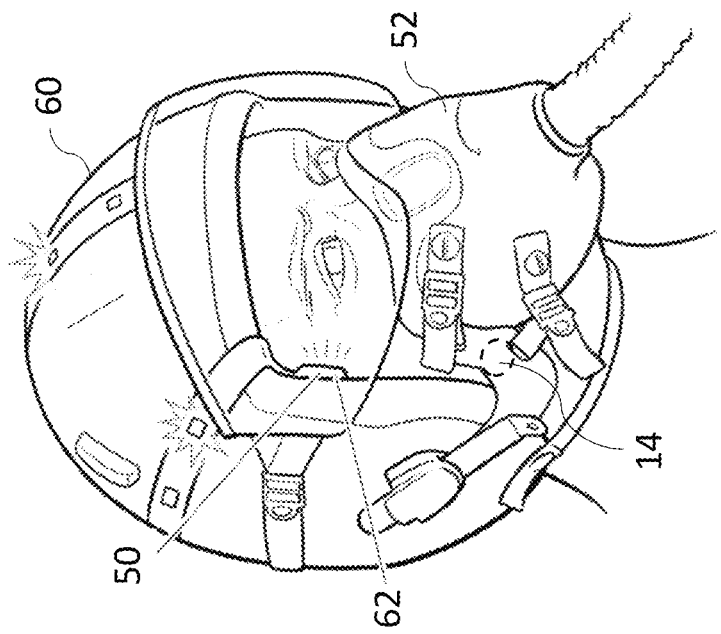
FIG. 4 illustrates an example of an activation accessory secured in a mask in accordance with an embodiment of the present invention.

In some cases, as shown in FIG. 4, the wearable module 14 may be supported in a mask 52 (e.g., a mask used by a firefighter, a diver, an aircrew member, of another wearer), where the mask 52 is configured to position the wearable module 14 so as to be overlying an area of the wearer's jaw or other portion of the wearer's head or face. Alternatively, as shown in FIG. 5, the wearable module 14 may have an adhesive applied to a surface thereof to enable the wearable module 14 to be worn on the face or head of the wearer (see, e.g., FIG. 6). Such an adhesive may, in one case, be in the form of a removeable film 54 adhered to the surface of the wearable module 14.

The wearable module 14 may include more than one sensor 16, with the multiple sensors arranged with respect to one another so as to permit individual and/or group activation thereof by associated volitional jaw motions of the wearer. For example, FIG. 7 illustrates a wearable module 14' that includes two sensors 16-1, 16-2. Each sensor 16-1, 16-2 may be a Hall effect sensor or other sensor and may be associated with a respective paddle switch 56-1, 56-2, which can be depressed through a volitional jaw motions of the wearer. Depressing a paddle switch will cause its associated sensor to be activated.

Further, as shown in FIGS. 1, 3, 4, and 6, in addition to the vibrational motor 12, a visual activation indicator 50 may be present. Such a visual activation indicator, e.g., one or more LEDs, may be coupled to receive a visual activation indication signal from the controller 18 (processor 22) and the processor-executable instructions stored in memory 26, when executed by processor 22, may further cause processor 22 to transmit the visual activation indication signal to the visual activation indicator 50 so as to illuminate the one or more LEDs for a brief period of time if/when the processor 22 determines that the input signals from the sensor 16 signals represent a command for the controlled device. As shown in the various illustrations, the visual activation indicator 50 may be located on the headset 44, on a helmet 60 or an indicator panel 62 associated therewith, or as an attachment, integral or otherwise, to a pair of glasses 64 or goggles, e.g., on the temple pieces 66 thereof. An activation indicator of this kind is especially useful when the wearable module 14 is used to control devices such as PTT controllers/adapters associated with tactical radios or the radios themselves. When providing microphone actuation when using such radios, a "microphone status LED" may be included in visual activation indicator 50 to provide a visual awareness of microphone condition. This LED emits light inside of the eyeglasses 64 which is visible only by the wearer. This provides effective light discipline in the tactical situations. Light would be visible when the microphone is in use (i.e., open) and would be extinguished when the microphone is not in use (i.e., off).

As discussed above, in various embodiments wearable module 14 is positioned so as to be flush against the wearer's face (or nearly so), over the jaw, masseter muscle, or other area of the wearer's face, so that clenching/flexing or other displacement of the jaw activates the sensor 16 to emit a signal to the processor 22. Power supply and control electronics for the wearable module 14 may be incorporated within the module itself, and/or in clothing, a frame, or a mask that supports the wearable module 14 or elsewhere. In the arrangement shown in FIG. 3, the wearable module 14 is mounted to the earphone cup 48 of headset 44 by means of a frame 46 about the circumference of the earphone cup. In alternative arrangements, such as those shown in FIGS. 8A-8D, the frame 46 may be mounted to the earphone cup 48 by means of friction fit frame 46-1, a frame 46-2, 46-3, 46-4 that is fitted by means of a screw 68, a rivet or pin 70, or other attachment means. In some embodiments, the wearable module 14 may be attached to or integrated in a moveable portion of mount 42 that is rotatable about a rivet, pin or other joint or hinge and may also be flexible so as to be moved adjacent to or away from a wearer's face. This is useful to prevent unwanted actuations of sensor 16. Such a moveable portion of mount 42 may be hingeably attached to a frame 46 by a spring-loaded hinge that keeps the wearable module 14 against the wearer's face even when the wearer moves his/her head unless moved away from the wearer's face by an amount sufficient to engage a detent that prevents return to a position adjacent a wearer's face unless manually adjusted by the wearer. Such a hingable arrangement may incorporate a spring-loaded hinge of any type, for example a spring-loaded piano hinge, butt hinge, barrel hinge, butterfly hinge, pivot hinge, or other arrangement.

Returning to FIG. 6, illumination element 50 can be attached to the inside of eyeglass temples 66 or slipped over a temple piece to contact the wearer's temple area when the eyeglasses are worn. This also provides a convenient location for vibration motor 12. From this position on the user, when the processor of wearable module 14 detects volitional facial movements of the wearer, such as clenching, flexing, or other displacement of the wearer's jaw, eyebrow, temple, etc., which is then turned into a command signal, for activating, deactivating, or controlling a controlled device (e.g., changing the volume of audio communications or music, turning on integrated lighting modules, or answering a phone call, the vibration motor 12 may be activated to provide feedback that indicates successful recognition of the input command. As discussed below, a distinct "language" (sometimes referred to below as a "clench language") may be programmed to control certain functions of the controlled device using specific masseter muscle clench (or other wearer jaw action(s)) sequences or patterns. The vibration motor 12 may also provide haptic feedback to the user as notification of microphone status or other enabled systems. For example, light vibrations of vibration motor 12 in a specific pattern may alert the wearer that a microphone is open, so as to prevent an "open-mic" situation where others are prevented from communicating over a common channel.

Further, additional sensors such as for wearer vital signs monitoring may also be integrated into the temple 66 to provide remote biomonitoring of the wearer, as the temple area has been proven to be an effective location for sensing certain vital signs. Such sensors may be integrated into the eyeglass temples 66, permanently attached as an accessory, or attached to the inside of the temple using adhesive tape, glue, magnets, hook and loop fasteners, screws, or a tongue and groove or dovetail profile connection mechanism. The sensor signal may be routed through a powered cable/tether or via a wireless connection such as Bluetooth or Near Field Magnetic Induction.

As should be apparent from the above discussion, use of the activation accessory does not require donning a headset or mask. Instead, the activation accessory can be worn by itself, e.g., through use of an adhesive. Incorporating the activation accessory in headsets would typically be the norm for any member of an aircraft flight or operations crew, but headsets such as the one illustrated in the above-referenced figures are not restricted to use by flight/aircraft crews and may be employed by ground forces, naval/coast guard personnel, and civilians. For example, headsets such as the ones described herein may be employed by workers in and around constructions sites, sports arenas, film and television production locations, amusement parks, and many other locations. By employing headgear equipped with activation accessories such as those described herein, wearers thereof have ready access to activation/deactivation/operation of illumination, imaging, gaming, and/or communications system(s)) in a hands-free fashion. Note that although FIG. 3 illustrates a headset with both left and right earphone cups, this is for purposes of example only and the present system may be used with headsets having only a single earphone cup, or one or two earpieces. Indeed, the present system may be used even with headgear that does not include any earphones or earpieces, for example attached to a band worn on the head or neck, or on a boom of a helmet or other headgear.

When assessing the input signals from the sensor(s) 16 for a signal pattern indicative of a plurality of volitional jaw motions of the wearer, the processor 22 may evaluate the input signals against a stored library of command signal representations, where each command signal representation characterizes an associated command for the controlled device. Alternatively, or in addition, the input signals may be assessed according to respective power spectral densities thereof within specified time periods. Or, in the case of Hall effect sensors in particular, the input signals may be assessed according to count values of the Hall effect sensor(s) received within a specified time period. Still further, the input signals may be evaluated against a trained model of command signal representations, where each command signal representation characterizes an associated command for the controlled device.

Figure 9:
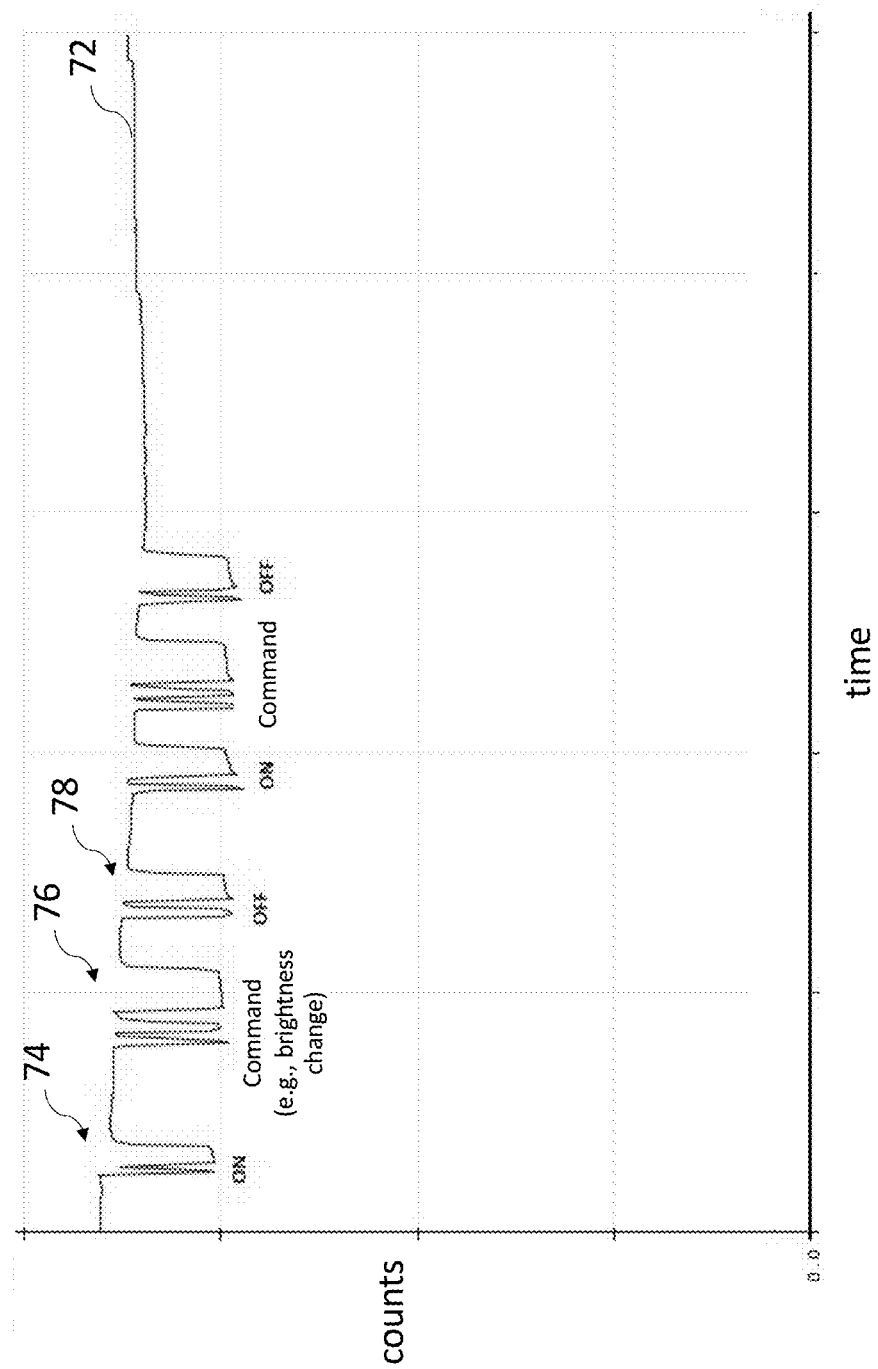
FIG. 9 illustrates an example of an input signal received by a processor of a wearable module from a sensor of the wearable module in accordance with embodiments of the present invention.

An example of an input signal received by processor 22 from sensor 16 is illustrated in FIG. 9. Trace 72 depicts "counts" of the Hall effect sensor 16 received by processor 22 over time. In this context, the counts, represent the applied magnetic field detected by the Hall effect sensor 16 which varies with the jaw clench actions of the wearer. Other output parameters of Hall effect or other sensors that can be measured to provide similar results include measures of voltages and/or currents output by sensors. More generally, in embodiments of the present invention the wearable module of the activation accessory 10 includes one or more switch elements (e.g., Hall effect sensor(s) or other(s) of the sensors discussed herein) that is/are sensitive to movements of a wearer's jaw or other muscle(s) and which are communicatively coupled to controller 18 having processor 22 and memory 26 coupled thereto and storing processor-executable instructions. Processor 22 is further coupled to provide an output signal to an indicator, such as illumination element 50 and/or vibration motor 12. The wearable module 16 may be fitted to a body-worn article (e.g., a headset, mask, eyeglasses/goggles, or other associated element) by an elongated member so as to be positionable to allow the one or more control surfaces associated with the one or more switch elements to contact a wearer at a desired location, or to observe/detect motion of a wearer's muscle(s). The processor-executable instructions stored in memory 26, when executed by processor 22, cause the processor to receive input signals from the one or more switch elements, detect relaxed (signal level high in FIG. 9) and clenched/flexed (signal level low) or other conditions (e.g., forwards and back or sideways displacement) of the wearer's muscle(s), e.g., by level or edge detection of the input signals. From these input signals, processor 22 decodes the relaxed and clenched/flexed conditions as commands (74, 76, 78, etc.) for controlling electronic system components communicatively coupled to the controller and alerts the wearer to successful decoding of the commands by providing the output signal to the indicator.

As illustrated in FIG. 9, trace 72 exhibits marked shifts in count values corresponding to periods of time when a wearer relaxes (signal level high) and clenches (signal level low) his/her jaw while wearing a wearable module 14. The detection of such actions by processor 22 may be edge-sensitive or level-sensitive. Further, as indicated above, the sensor signals may be decoded according to a language to discriminate between activation, deactivation, and operational commands for the controlled device. The example shown in FIG. 9 represents decoded signals representing commands for an illumination unit. Signal groups 74 and 78, a short clench followed by a long clench, represent activation ("on") and deactivation ("off") commands. That is, the illumination module is ordered to change operating state, from a current state on or off to an opposite state off or on, respectively, when such a set of input signals is recognized by the processor 22. Signal group 76 represents a command to alter an output characteristic, e.g., brightness, and corresponds to two short clenches followed by a long clench. The two short clenches signal a change in output and the long clench signals that the brightness of the illumination unit should be varied, e.g., low to high, during the period of the clench action. Of course, other clench languages for a variety of controlled devices and sensor-muscle arrangements may be implemented. For example, in addition to double clench/flex inputs signaling a following command input, triple clench/flex inputs may be recognized as signaling valid command inputs, different from commands associated with a double clench input. Further multiple clench inputs and/or clench-and-hold inputs may also be recognized as signifying different commands. Such multi-clench/flex inputs are useful for eliminating unintentional actuations of sensor 16, as may be occasioned by involuntary muscle movements or by a wearer chewing food, gum, etc., or clenching/flexing his/her jaw during other activities. Generally, the intended command may be identified by decoding the detected relaxed and clenched/flexed conditions of the wearer's muscles according to a language that identifies such commands according to a number of detected clench/flex actions identified within a time period, for example, a number of detected short and long (e.g., clench/flex-and-hold) actions identified within a time period. Valid forms of clench/flex inputs may be used to turn on/off lighting elements and/or individual LEDs thereof, adjust the intensity of one or more illuminated LEDs, or to signal other desired operations. In general, clench/flex input actuation sequence timings, repetitions, and durations may each be used, individually and/or in combination to specify different command inputs for one or more controlled devices.

Figure 10:
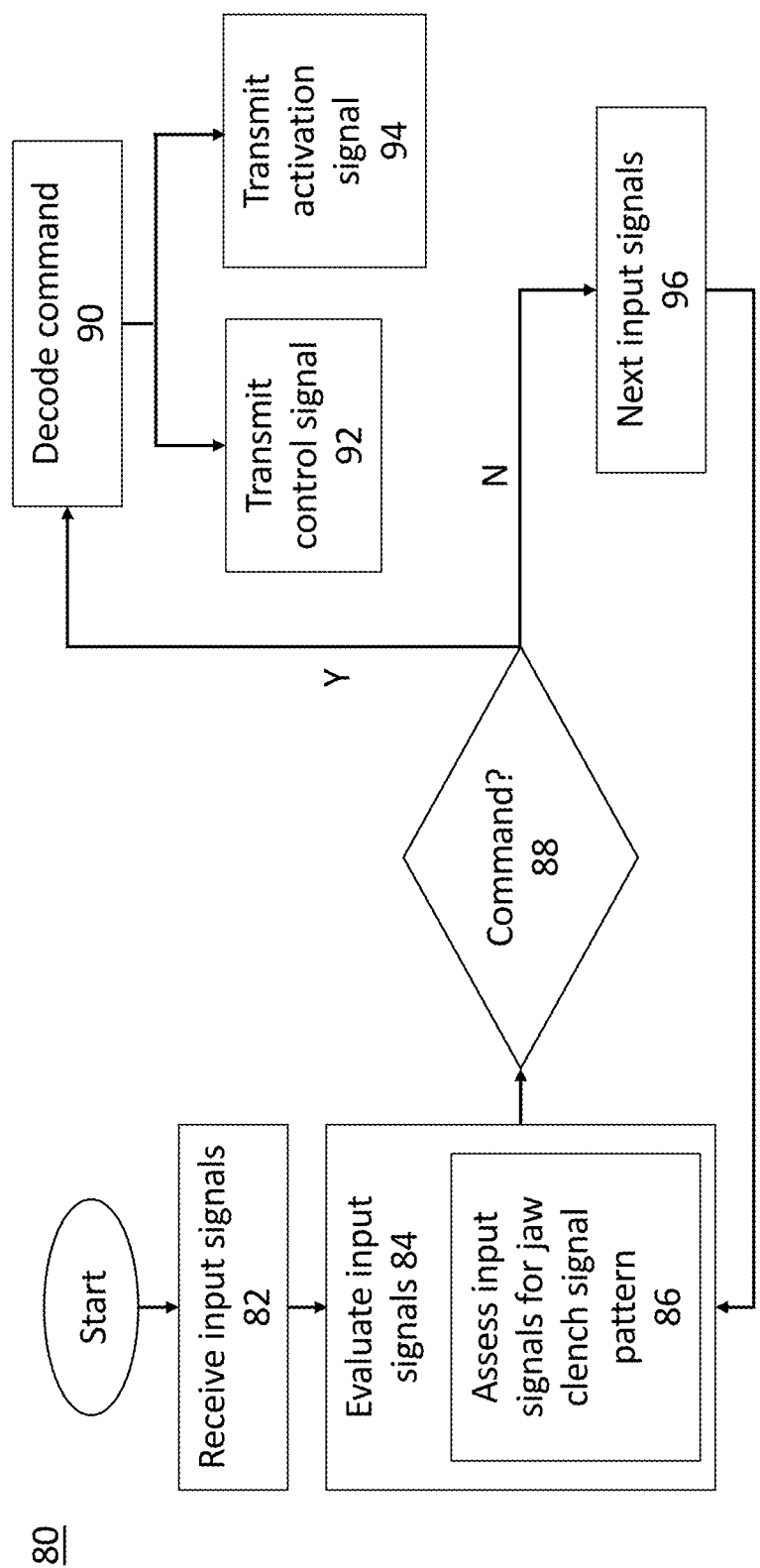
FIG. 10 illustrates a method of operating a controlled device in a hands-free manner through volitional muscle actions of a wearer in accordance with an embodiment of the invention.
Figure 11B:
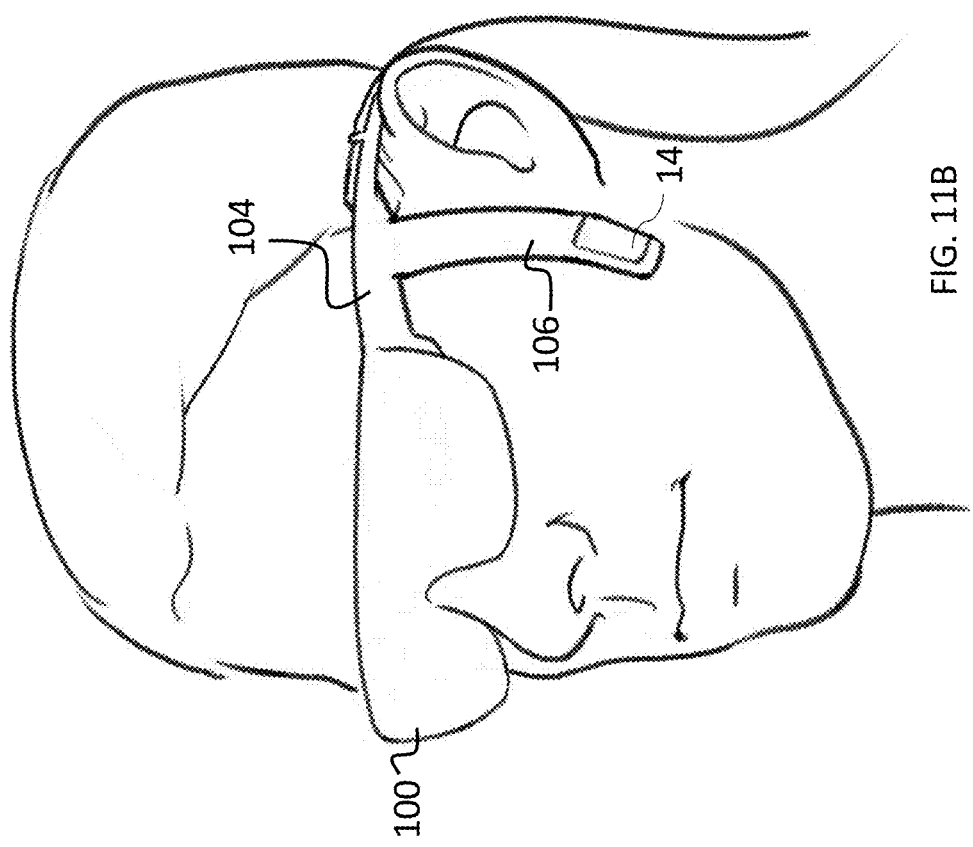
FIGS. 11A-14B illustrate various embodiments of head-worn visioning devices with wearable modules configured in accordance with embodiments of the present invention.
Figure 11A:
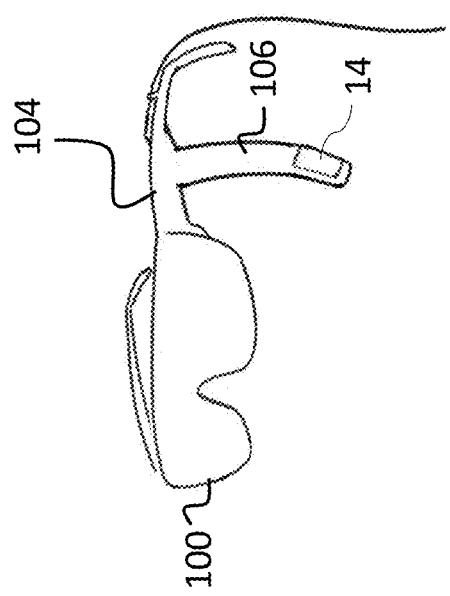
Figure 12B:
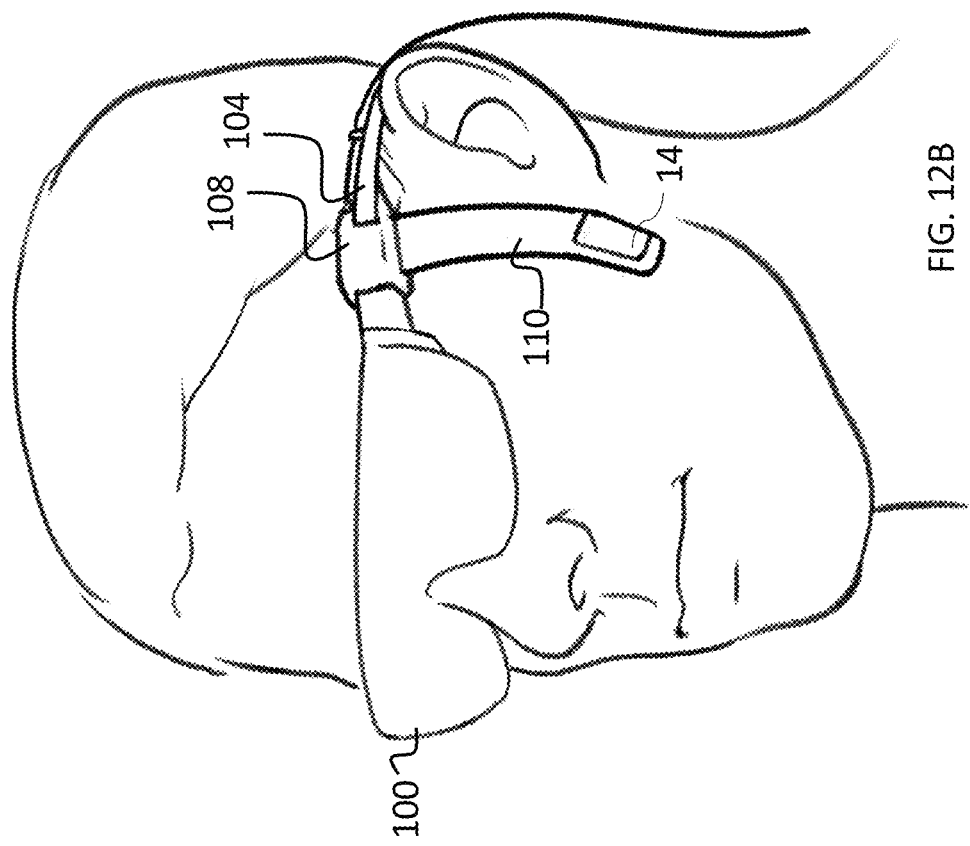
Figure 12A:
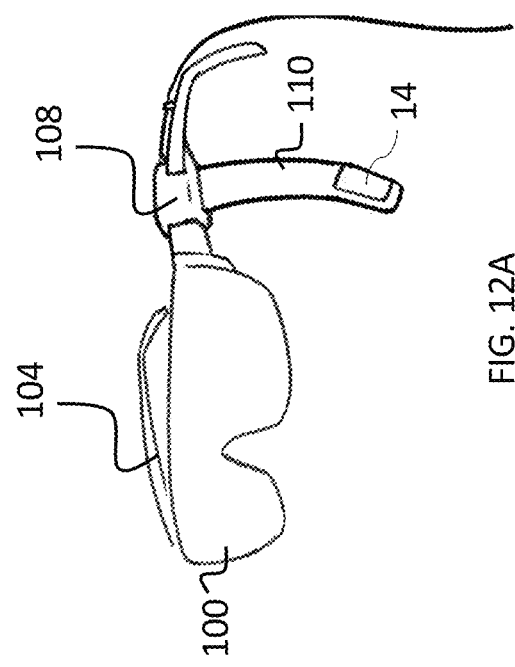
Figure 13B:
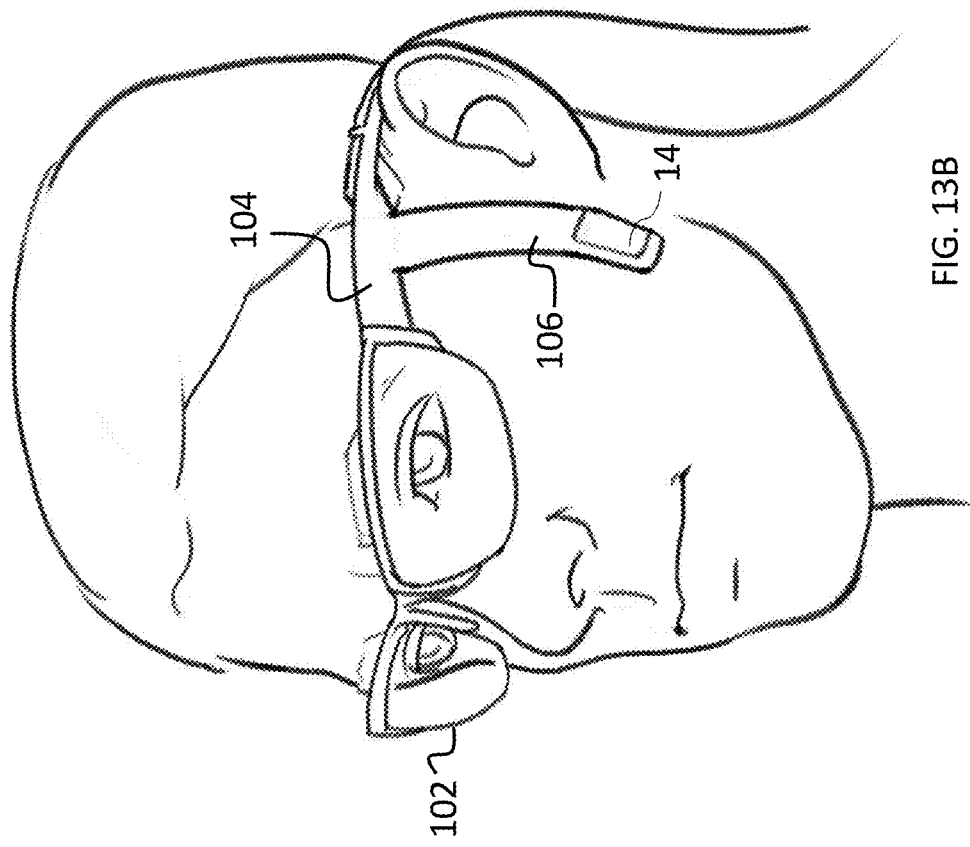
Figure 13A:
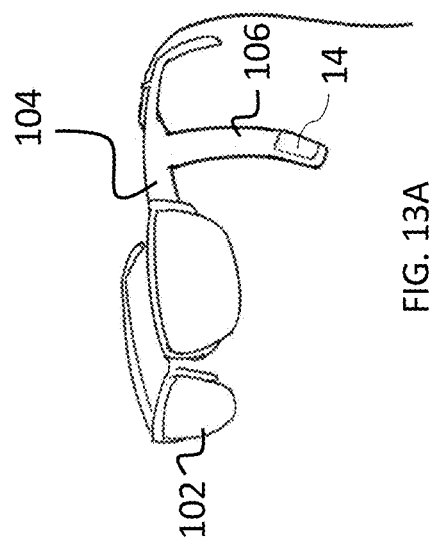
Figure 14B:
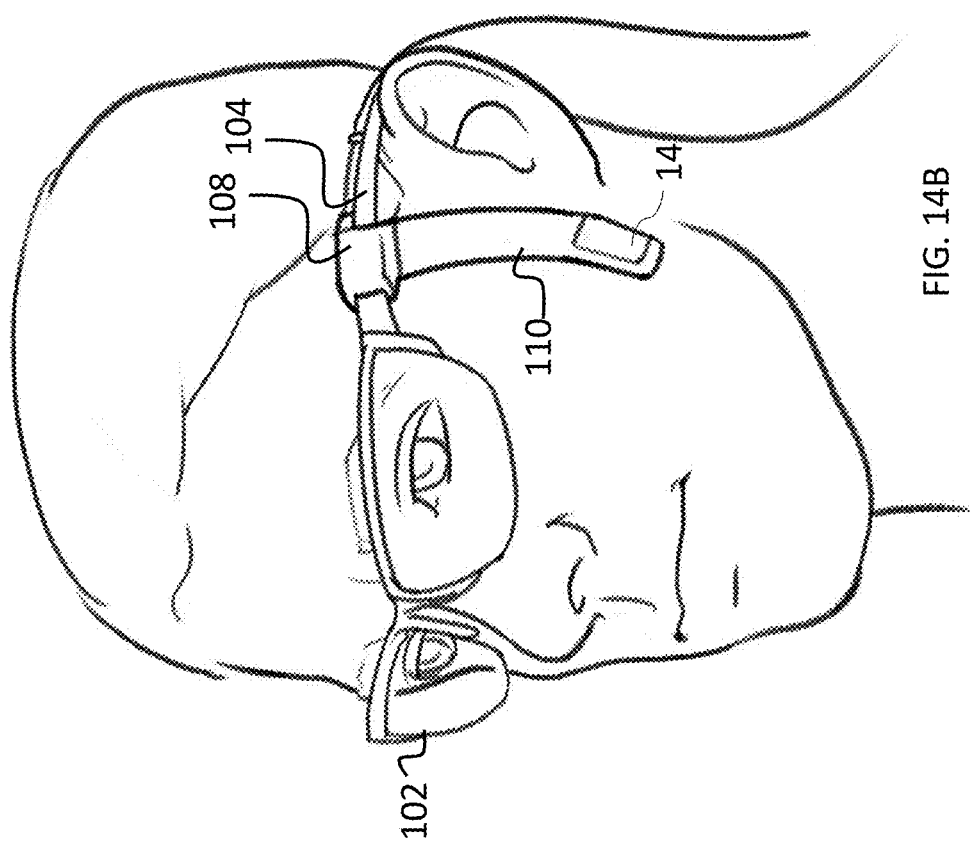
Figure 14A:
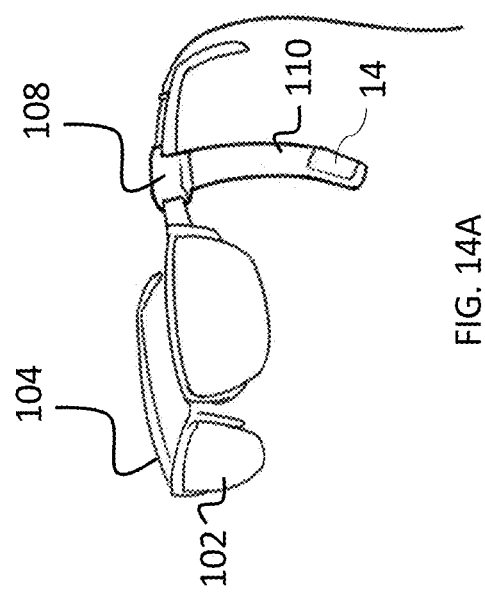

FIG. 10 illustrates a method 80 of operating a controlled device in accordance with embodiments of the present invention. At 82, the controller 18 receives from the sensor 16 in the wearable module 14 communicably coupled to the controller, first input signals. At 84, processor 22 of controller 18 evaluates the first input signals according to and by executing processor-executable instructions stored in memory 26 to determine whether or not the first input signals represent a command for the controlled device. As discussed above, this evaluation 84 proceeds by the processor assessing 86 the first input signals for a signal pattern indicative of a plurality of volitional jaw motions of a wearer of the wearable module 14. If processor 22 determines that the first input signals represent the command, step 88, then processor 22 decodes the command 90, e.g., by identifying the input signals as being one of a number of patterns of a language, as described above, and transmitting 92 an associated control signal to the controlled device via a communication element communicably coupled to the processor, and optionally transmitting 94 an activation signal to a vibration motor of the wearable module. As indicated above, the communication element may be a cable having a plug configured to mate with a jack at the controlled device, a transmitter adapted for radio frequency communication with a receiver at the controlled device, or other element. Decoding the command signal may involve determining the number of short clench/flex actions preceding a long clench/flex action to determine the nature of a following one or more long and/or short clench/flex actions, and may also depend on a current operating state of the controlled device. Otherwise, step 96, the processor 22 does not transmit the control signal and the activation signal and instead proceeds to evaluate second/next input signals 96 from the sensor in a like manner as the first input signals.

In general, sensor 16 is a device that requires little or no mechanical displacement of a control element in order to signal or effect a change (or desired change) in state of a controlled system. One example of such a device is a Hall effect sensor. Other examples of such a device include an EMG sensor or a piezo switch, such as the Piezo Proximity Sensor produced by Communicate AT Pty Ltd. of Dee Why, Australia, a tape switch, a fabric switch, or other switch that requires little or no mechanical displacement of a control element. Piezo switches generally have an on/off output state responsive to electrical pulses generated by a piezoelectric element. The electrical pulse is produced when the piezoelectric element is placed under stress, for example as a result of compressive forces resulting from a wearer clenching his/her jaw so that pressure is exerted against the switch. Although the pulse is produced only when the compressive force is present (e.g., when the wearer's jaw or other muscle is moved), additional circuitry may be provided so that the output state of the switch is maintained in either an "on" or an "off" state until a second actuation of the switch occurs. For example, a flip-flop may be used to maintain a switch output logic high or logic low, with state changes occurring as a result of sequential input pulses from the piezoelectric element. One advantage of such a piezo switch is that there are no moving parts (other than a front plate that must deform by a few micrometers each time a wearer's jaw is clenched) and the entire switch can be sealed against the environment, making it especially useful for marine and/or outdoor applications.

Another example is a micro tactile switch. Although tactile switches employ mechanical elements subject to wear, for some applications they may be more appropriate than Hall effect sensors or piezo switches because they provide mechanical feedback to the user (although the haptic feedback provided by vibration motor 12 also provides an acceptable level of feedback for a user and so may be sufficient in the majority of instances). This feedback can provide assurance that the switch has been activated or deactivated. Momentary contact tactile switches may also be used, but because they require continual force (e.g., as provided by clenching one's jaw against the switch), they are best suited to applications where only a momentary or short engagement of the active element under the control of switch is desired, for example, signal light flashes, burst transmissions, or other short duration applications, or where a flip flop is used to maintain an output state until a subsequent input is received, as discussed above. Other forms of switches include a ribbon switch (e.g., as made by Tapeswitch Corporation of Farmingdale, NY) and conductive printed circuit board surface elements activated via carbon pucks on an overlaid keypad.

Still other embodiments of a sensor 16 include those that do not require any physical contact with the wearer's jaw, etc. For example, sensor 16 may be any of an ultrasonic motion sensor, a camera or LIDAR unit, a motion sensor (e.g., employing one or more light emitting diodes for detection of motion), a laser sensor such as a vertical cavity surface emitting laser (VCSEL) sensor, or, more generally, a time of flight sensor that uses optical and/or acoustic means to detect motion. Or, sensor 16 may be another form of proximity or motion sensor. In such cases, sensor 16 need only be positionable so as to be able to detect movement, e.g., clenching, flexing, and/or lateral displacement, of the user's jaw, temple, eyebrow, chin, or other aspect of the user's head or face. For example, sensor 16 may be located on a headset, eyeglasses, or other element worn by the user and oriented such that it can observe such movement.

Further, in various embodiments, the controlled device may consist of one or more LEDs, which emit light in one or more wavelengths. Further, the controlled device may include one or more cameras for digital still and/or video imaging. In some instances, a lighting element may be worn on one side of the headset while an imaging system is worn on the opposite side, each being controlled by separate activation accessories mounted on respective opposite sides of the headset, or by activation accessory if the lighting and illumination systems are responsive to different command signals, similar to the way in which computer cursor control devices (e.g., touch pads, mice, etc.) may be separately responsive to single, double, triple, or other multiple clicks. Indeed, the activation accessory may itself be used to control a cursor as part of a user-computer interface. For example, any or all of cursor type, cursor movement, and cursor selection may be controlled using a wearable module 14. Applications for such uses include computer gaming interfaces, which today commonly include head-worn communication equipment. One or more wearable modules 14 configured in accordance with embodiments of the invention may be fitted to such headgear (either when manufactured or as an after-market addition) to provide cursor control capabilities. Conventional wired or wireless communication means may be employed to provide a connection to a console, personal computer, tablet, mobile phone, or other device that serves as the gaming or other host. The use of such human-machine interfaces may find particular application for users that have no or limited use of their hands and afford them a convenient means of interacting with a personal computer, tablet, mobile phone, or similar device.

Further, the controlled device(s) may include one or more microphones. Such microphones may be mounted or integral to a headset and make use of bone conduction transducers for transmission of audio signals. Alternatively, or in addition, wearable module 14 may be used to adjust the presence, absence, and/or volume of audio played through one or more earphones or other earpieces. Also, a wearable module 14 may be used to control off-headset equipment, for example, via a wireless transmitter.

One or more of the above-described embodiments may permit signal generation via a control surface that can be activated by direct or indirect force, hinged paddle, touch-sensitive surface, or other tactile actuation device. Devices configured in accordance with these embodiments may employ moveable structures (e.g., paddles) that house sensors to detect a change in an electromagnetic field when a corresponding magnet is moved in proximity to the sensor. Such devices may be in the form of an accessory to a remote (e.g., hand-held) device or fully integrated into a wearable form factor such as eyeglasses and headsets. Other sensors, as discussed herein, may also be used.

By providing both a left and right activation means (or any number of them) which may be configured to allow for input of various kinds (e.g., different numbers of activations similar to single-, double- or other mouse clicks), a user may provide different commands for an associated device. For example, different command activation sequences may be used for zooming a camera, panning a direction in a virtual/visual environment, or a host of other commands to control cameras, audio transmissions (volume up or down), etc. And, in connection with cursor control actions of a computer system or similar device (including but not limited to mobile phones, tablets, etc.), command sequences for swiping between views/screens, advancing or repeating tracks (music, video, or audio/video), active windows on a screen, etc. may be accommodated. In addition to the foregoing, the use of gyros and/or accelerometers while clenching and holding can allow for selecting and moving objects in the virtual field. This is similar to a click-and-hold followed by movement of a cursor with a mouse or joystick in that it allows a user to move objects (e.g., icons) around on a virtual desktop, to open menus, and to select commands, etc. by clenching and moving one's head. The gyros and/or accelerometers may be incorporated in wearable module 14 or elsewhere (e.g., in a frame supporting the wearable module).

In addition to or as an alternative to gyros and/or accelerometers embodiments of the present invention, whether instantiated as head-worn devices, augmented reality/virtual reality headsets, or others, may employ the present systems and methods for operating a controlled device in a hands-free manner through volitional muscle movements of a wearer, and in particular an activation accessory for a controlled device that includes a sensor configured to detect a relaxed condition and a flexed condition of one or more muscles associated with clenching, flexing, and/or lateral displacement of a wearer's body part or displacement of the wearer's body part itself, together with input means such as tactile buttons and switches, touch activated control surfaces, and gesturing technologies, that might also rely on head and eye tracking technologies, as means of controlling their operation. For example, eye tracking technologies that respond to a user gazing at a particular object as a signal for moving a cursor or other controlled item to a location denoted by the user's gaze may be used in combination with the activation accessory such that the activation accessory can be employed to effect a selection, select and hold, and/or other control operation of a screen element at a screen location denoted by the user's gaze.

Referring now to FIGS. 11A-14B, various embodiments of head-worn visioning devices with wearable modules 14 are illustrated. Such head-worn visioning devices are suitable for application in a variety of contexts, including military, law enforcement, health care, field repair, and others (e.g., consumer). Unlike hand-held and/or hand operated visioning devices, which typically require the user to use his or her hands to operate a control unit or console, visioning devices configured in accordance with embodiments of the present invention can be operated in a hands-free fashion and worn with or without a helmet or other headdress, communication devices, etc. In addition to the visioning means, the frame carrying the visioning means provides a platform for audio/video capture and/or communications. For example, one or more speakers, ear buds, and/or microphones may be provided integral to or attached to the frame. Hands-free operation of the visioning devices is facilitated using a wearable module 14 that includes a clench switch as described above that can be activated when the user clenches or otherwise manipulates his/her jaw, temple, etc.

FIGS. 11A-11B and 12A-12B illustrate embodiments of a visioning device in the form of head-worn virtual reality goggles 100 with integrated wearable modules 14 (FIGS. 11A-11B) and attachable wearable modules 14 (FIGS. 12A-12B) configured in accordance with the present invention. FIGS. 13A-13B and 14A-14B illustrate embodiments of a visioning device in the form of head-worn augmented reality glasses 102 with integrated wearable modules 14 (FIGS. 13A-13B) and attachable wearable modules 14 (FIGS. 14A-14V) configured in accordance with the present invention. As shown, the various visioning devices each include a frame 104 worn over the ears.

In some instances, visioning devices 100, 102 may be personalized to a wearer by creating a model, either physical or digital, of the wearer's head and face and fabricating an visioning device 100, 102 (or just a frame 104) specifically to suit the wearer according to the dimensions provided from the model. Modern additive manufacturing processes (commonly known as 3D printing) make such customizations economically feasible even for consumer applications and visioning devices 100, 102 (or just frames 104) could readily be produced from images of a wearer's head and face captured using computer-based cameras and transmitted to remote server hosting a Web service for purchase of the visioning device(s) (or frames). For example, following instructions provided by the Web-based service, a user may capture multiple still images and/or a short video of his/her head and face. By including an object of known dimensions (e.g., a ruler, a credit card, etc.) within the field of view of the camera at the approximate position of the user's head as the images are captured, a 3D model of the user's head and face can be created at the server. The user can then be provided with an opportunity to customize a visioning device 100, 102 (or frame 104) to be sized to the dimensions of the model, selecting, for example, color, materials, the positions over the ears, etc. at which the visioning device 100, 102 will be worn. Once the customizations are specified, and payment collected, the visioning device specification may be dispatched to a manufacturing facility at which the visioning device is fabricated.

Visioning devices 100, 102 may further support one or more communication earpieces (not shown) and/or one or more microphones (not shown), the earpiece(s) and microphone(s) allowing for communications to/from the wearer. The earpiece(s) and microphone(s) may be communicatively connected to a transceiver carried elsewhere on the wearer's person, either using wired or wireless connections. In other embodiments, the earpiece(s) and/or microphone(s) may be eliminated, and audio communications facilitated through bone conduction elements. Portions of the illumination devices 100, 102 are in contact with the wearer's head. Hence, rather than an earpiece, a bone conduction headphone that decodes signals from a receiver and converts them to vibrations can transmit those vibrations directly to the wearer's cochlea. The receiver and bone conduction headphone(s) may be embedded directly in the visioning device 100, 102, or in some cases the receiver may be external thereto. One or more bone conduction headphones may be provided. For example, the headphone(s) may be similar to bone conduction speakers employed by scuba divers and may consist of a piezoelectric flexing disc encased in a molded portion of the visioning device 100, 102 that contacts the wearer's head just behind one or both ears. Similarly, a bone conduction microphone may be provided.

Although not shown in the various views, a power source for the electronics is provided and may be housed within the visioning device 100, 102 or located external thereto (e.g., worn on a vest or belt pack). In some cases, a primary power source may be located external to the visioning device 100, 102 and a secondary power source provided integral thereto. This would allow the primary power source to be decoupled from the visioning device 100, 102 which would then revert to using the secondary power source (e.g., a small battery or the like), at least temporarily. To facilitate this operation, the visioning device 100, 102 may be provided with one or more ports allowing connection of different forms of power supplies. Also, status indicators (e.g., LEDs or other indicators) may be provided in to provide information concerning the imaging elements, communication elements, available power, etc. In some embodiments, haptic feedback may be used for various indications, e.g., low battery, etc.

Frames 104 of various visioning devices 100, 102 may be fashioned from a variety of materials, including but not limited to plastics (e.g., zylonite), metals and/or metal alloys, carbon fiber, wood, cellulose acetates (including but not limited to nylon), natural horn and/or bone, leather, epoxy resins, and combinations of the foregoing. Fabrication processes include, but are not limited to, injection molding, sintering, milling, and die cutting. Alternatively, or in addition, one or more additive manufacturing processes, such as extrusion, vat photopolymerization, powder bed fusion, material jetting, or direct energy jetting, may be used to fashion the illumination device and/or components thereof.

Activation/deactivation and/or other operation of the imaging elements, and/or audio communication elements of the visioning devices 100, 102 may be effected through the use of integrated wearable modules 14 or attachable wearable modules 14, as applicable. Each of which may include a sensor of any of the kinds discussed above. The sensor is responsive to minimal displacements of the wearer's jaw, temple, or other facial element, which the sensor is positioned on, near, or so as to observe when the associated visioning device 100, 102 is worn, e.g., overlying the area of the user's jaw when the visioning device 100, 102 is worn, so that clenching, flexing, or other displacement of the wearer's jaw (or similar movement) causes the sensor to signal such movement. The use of a such a sensor allows for hand-free operation of the imaging elements (and, optionally, other elements) of the device.

In visioning devices 100, 102 an integrated wearable module 14 is included at or near the end of a frame element 106 that is a molded component of the original frame 104, with the wearable module 14 being positioned by the frame element 106 so as to be flush against the wearer's face (or nearly so) over the wearer's jaw when the visioning device 100, 102 is worn so that clenching, flexing, or other displacement of the wearer's jaw causes the sensor in the wearable module to signal such movement. In visioning devices 100, 102 that do not include an integrated wearable module 14, an attachable wearable module 14 may be provided. The attachable wearable module 14 include a buckle 108 that slides over a temple piece of frame 104 and an elongated member 110 that extends down from the temple piece to the area of the wearer's face near the jaw line so that the sensor included in the wearable module 14 at or near the end of the elongated member 110 is positioned over the wearer's jaw. Thus, the attachable wearable module 14 may be provided as an after-market accessory for a visioning device 100, 102 not originally fitted with hands-free operating means. Whether included as a component of an attachable wearable module or an integrated wearable module, the position of the wearable module 14 may be adjustable, e.g., by providing a telescoping elongated member 110 or frame element 106, as applicable. In this way, the sensor may be positioned at various distances from temple pieces of frame 104, so as to accommodate wearer's faces of different sizes.

As should be immediately apparent from these illustrations, use of wearable module 14 allows activation/deactivation of the imaging elements, communications elements, and/or other elements of visioning devices 100, 102 in a hands-free fashion. In some instances, elements of visioning devices 100, 102 may be controlled using wearable modules 14 positioned on different sides of the wearer's face or by a single wearable module 14 where the sensors are responsive to multi-clench (or other displacements) actuations of wearable modules 14, as described above. In some embodiments, the wearable module 14 may be hingeably attached to frame 104. This is useful to prevent unwanted actuations of the sensor in that it can be moved away from or adjacent to the wearer's face as required. Such a hinge arrangement may include a spring-loaded hinge that keeps the switch against the wearer's face even when the wearer moves his/her head unless moved away from the wearer's face by an amount sufficient to engage a detent that prevents return to a position adjacent a wearer's face unless manually adjusted by the wearer. The hingable arrangement of wearable module 14 may involve a spring-loaded hinge of any type, for example a spring-loaded piano hinge, butt hinge, barrel hinge, butterfly hinge, pivot hinge, or other arrangement.

Thus, systems and methods for operating a controlled device in a hands-free manner through volitional jaw clench actions and/or other muscle movements of a wearer, and in particular using an activation accessory for a controlled device that includes a sensor configured to detect a relaxed condition and a flexed condition of one or more of the wearer's muscles, e.g., muscles associated with clenching, flexing, and/or lateral or other displacement of a wearer's jaw, have been described.

What is claimed is:

1. A module for a wearable article, the module comprising:
   a switch coupled to provide a first input signal to a controller, the switch including a control surface positionable on or near a wearer's face or head when the wearable article is worn and the switch configured to provide the first input signal when the switch is activated by muscle movement of the wearer;
   a microphone coupled to provide a second input signal to the controller; and
   the controller coupled to receive the first and second input signals, and configured to:
      evaluate the first and second input signals to determine whether or not the first input signal represents a command for a controlled device by:
         assessing the second input signal to determine if the muscle movements are associated with wearer speech and, if so, ignoring the first input signal and proceeding to evaluate further first and second input signals,
         otherwise assessing the first input signal as indicative of the command for the controlled device, decoding the command, and transmitting, via a communication element coupled to the controller, a control signal for the controlled device,
         wherein the controller is configured to distinguish the command for the controlled device from wearer speech by at least one of: assessing said second input signal using a threshold filter to distinguish the wearer speech, or by evaluating spectral content of the second input signal.

2. The module for a wearable article of claim 1, wherein the wearable article is a pair of eyeglasses and the module is adapted to be positioned on a temple piece of the eyeglasses.

3. The module for a wearable article of claim 1, wherein the controller is configured to control operation of the controlled device responsively to different actuations of the switch.

4. The module for a wearable article of claim 1, wherein the controller is configured to distinguish the command for the controlled device from wearer speech by additionally detecting signals indicative of wearer vocal cord activation when forming the wearer speech from an additional sensor.

5. A pair of eyeglasses including a switch, a controller, and a microphone, the switch coupled to provide a first input signal to the controller responsive to a control surface of the switch being displaced by muscle movement of a wearer of the eyeglasses, the microphone coupled to provide a second input signal to the controller, and the controller configured to evaluate the first and second input signals to determine whether or not the first input signal represents a command for a controlled device by:
   assessing the second input signal to determine if the muscle movements are associated with wearer speech and, if so, ignoring the first input signal and proceeding to evaluate further first and second input signals,
   otherwise assessing the first input signal as indicative of the command for the controlled device, decoding the command, and transmitting, via a communication element coupled to the controller, a control signal for the controlled device,
   wherein the controller is configured to distinguish the command for the controlled device from wearer speech by at least one of: assessing said second input signal using a threshold filter to distinguish the wearer speech, or by evaluating spectral content of the second input signal.

6. The pair of eyeglasses of claim 5, wherein the control surface of the switch is located in a nosepiece of the eyeglasses.

7. The pair of eyeglasses of claim 5, wherein the control surface of the switch is located on a temple piece of the eyeglasses.

8. The pair of eyeglasses of claim 5, wherein the controller is configured to control operation of the controlled device responsively to different actuations of the switch.

9. A head-worn visioning device including a switch, a controller, and a microphone, the switch coupled to provide a first input signal to the controller responsive to a control surface of the switch being displaced by muscle movement of a wearer of the head-worn visioning device, the microphone coupled to provide a second input signal to the controller, and the controller configured to evaluate the first and second input signals to determine whether or not the first input signal represents a command for a controlled device by:
   assessing the second input signal to determine if the muscle movements are associated with wearer speech and, if so, ignoring the first input signal and proceeding to evaluate further first and second input signals,
   otherwise assessing the first input signal as indicative of the command for the controlled device, decoding the command, and transmitting, via a communication element coupled to the controller, a control signal for the controlled device,
   wherein the controller is configured to distinguish the command for the controlled device from wearer speech by at least one of: assessing said second input signal using a threshold filter to distinguish the wearer speech, or by evaluating spectral content of the second input signal.

10. The head-worn visioning device of claim 9, wherein the control surface of the switch is located in a nosepiece of the head-worn visioning device.

11. The pair of eyeglasses of claim 9, wherein the control surface of the switch is located on a temple piece of the eyeglasses.

12. The head-worn visioning device of claim 9, wherein the controller is configured to control operation of the controlled device responsively to different actuations of the switch.

* * * * *